United States Patent
Li et al.

(10) Patent No.: US 11,883,033 B2
(45) Date of Patent: Jan. 30, 2024

(54) LEFT ATRIAL APPENDAGE OCCLUDER, AND METHOD OF APPLICATION

(71) Applicant: SHANGHAI PUSH MEDICAL DEVICE CO., LTD., Shanghai (CN)

(72) Inventors: Rui Li, Shanghai (CN); Shanshi Gong, Shanghai (CN)

(73) Assignee: SHANGHAI PUSH MEDICAL DEVICE CO., LTD., Shanghai (CN)

( * ) Notice: Subject to any disclaimer, the term of this patent is extended or adjusted under 35 U.S.C. 154(b) by 0 days.

(21) Appl. No.: 18/035,523

(22) PCT Filed: Dec. 31, 2020

(86) PCT No.: PCT/CN2020/142578
§ 371 (c)(1),
(2) Date: May 5, 2023

(87) PCT Pub. No.: WO2022/095268
PCT Pub. Date: May 12, 2022

(65) Prior Publication Data
US 2023/0389931 A1    Dec. 7, 2023

(30) Foreign Application Priority Data
Nov. 6, 2020    (CN) .......................... 202011226887.8

(51) Int. Cl.
*A61B 17/12*    (2006.01)
*A61B 17/00*    (2006.01)

(52) U.S. Cl.
CPC .... *A61B 17/12122* (2013.01); *A61B 17/0057* (2013.01); *A61B 2017/00592* (2013.01)

(58) Field of Classification Search
CPC .......... A61B 17/12122; A61B 17/0057; A61B 17/12031; A61B 17/12168;
(Continued)

(56) References Cited

U.S. PATENT DOCUMENTS

| 2020/0038004 A1 | 2/2020 | Corcoran et al. |
| 2021/0369283 A1* | 12/2021 | O'Halloran ...... A61B 17/12172 |
| 2023/0285029 A1* | 9/2023 | Yang ................ A61B 17/12168 |
| | | 606/1 |

FOREIGN PATENT DOCUMENTS

| CN | 105054980 A | 11/2015 |
| CN | 106466196 A | 3/2017 |

(Continued)

*Primary Examiner* — Jon Eric C Morales
(74) *Attorney, Agent, or Firm* — Bayramoglu Law Offices LLC

(57) ABSTRACT

A left atrial appendage (LAA) occluder, and a method of application are provided. The LAA occluder includes a plugging portion, a connecting portion, and a covering portion that are connected sequentially along an axial direction, where the plugging portion includes a first support mesh that can be transformed to have a reduced radial profile, and a first gathering member; a plurality of anchoring members for grasping LAA tissues are arranged on an outer peripheral surface of the first support mesh; the first gathering member is detachably connected to the connecting portion, such that the plugging portion can be provided individually at an LAA; the covering portion includes a second support mesh that can be transformed to have a reduced radial profile, and a second gathering member; and the second gathering member is provided at an end of the second support mesh away from the connecting portion.

19 Claims, 22 Drawing Sheets

(58) Field of Classification Search
CPC .... A61B 17/12172; A61B 2017/00035; A61B 2017/00084; A61B 2017/00893; A61B 2017/12095; A61B 2018/00351; A61B 2018/00613; A61B 2018/00839; A61B 2560/021

See application file for complete search history.

(56) References Cited

FOREIGN PATENT DOCUMENTS

| | | |
|---|---|---|
| CN | 106923883 A | 7/2017 |
| CN | 206792446 U | 12/2017 |
| CN | 109124755 A | 1/2019 |
| CN | 109662745 A | 4/2019 |
| CN | 210990532 U | 7/2020 |
| CN | 211560185 U | 9/2020 |
| CN | 112022246 A | 12/2020 |
| EP | 2363075 A1 | 9/2011 |
| WO | 2020123386 A1 | 6/2020 |

* cited by examiner

LEFT ATRIAL APPENDAGE OCCLUDER, AND METHOD OF APPLICATION

CROSS REFERENCE TO THE RELATED APPLICATIONS

This application is the national phase entry of International Application No. PCT/CN2020/142578, filed on Dec. 31, 2020, which is based upon and claims priority to Chinese Patent Application No. 202011226887.8, filed on Nov. 6, 2020, the entire contents of which are incorporated herein by reference.

TECHNICAL FIELD

The present disclosure relates to the field of medical devices, and in particular to a left atrial appendage (LAA) occluder, and a method of application.

BACKGROUND

Percutaneous left atrial appendage occlusion (LAAO) treatment is to deliver and release an LAA occluder to the LAA in the left atrium (LA) of the heart with an elongated delivery sheath through percutaneous puncture. The blood flow between LAA and LA is therefore blocked. And the thrombus which is commonly formed in the LAA of atrial fibrillation (AF) patients is prevented from entering the blood circulation system, thereby preventing atrial fibrillation (AF)-induced thromboembolism. Since 2001, the percutaneous LAAO treatment has been used clinically. Evidences of clinical use demonstrate that the percutaneous LAAO treatment can effectively reduce the risk of stroke of the AF patients.

In the prior art, an LAA occluder is commonly made of Nitinol alloy and polymer membrane. The Nitinol alloy normally functions as fixation framework, and the polymer membrane mainly functions as blood flow block.

Typically, there are plug-like LAA occluders and double-disc LAA occluders. A double-disc LAA occluder including a cover disc and a plug is more practical in clinic, because it can be repeatedly retracted and released from the sheath. However, the anatomies of LAA vary due to individual differences. According to clinical practices, common complexities after LAAO include: (1) The plug-like occluder could easily leave a residual cavity near the LAA opening, where thrombus could still easily happen. (2) With the double-disc occluder, while the plug is normal, the cover disc may impact the function of tissues nearby such as mitral valves. Or the plug may not function well. Most of the above conditions are ascribed to matching issue of the existing device with quite proportion of LAA. Hence, a novel model of LAA occluder needs to be designed to improve the above conditions. A LAA occluder could be selected more specifically to fit in the LAA anatomy in a surgery. Thereby, the LAA occluders will be more adaptive for various LAA anatomies. The scope of application of percutaneous LAAO treatment will be further expanded.

Therefore, the present disclosure provides an LAA occluder that is more flexible and adaptive to various LAA anatomies.

SUMMARY

In view of the above defects in the prior art, the present disclosure provides an LAA occluder, and a method of application. The LAA occluder is more flexible and adaptive to various LAA anatomies.

The present disclosure provides the following technical solutions. An LAA occluder includes a plugging portion, a connecting portion, and a covering portion, which are connected axially. The plugging portion includes a first support mesh that can be transformed to have a reduced radial profile, and a first gathering member. A plurality of anchoring members for grasping LAA tissues are arranged on an outer peripheral surface of the first support mesh. The first gathering member is provided at an end of the first support mesh close to the connecting portion. The first gathering member is detachably connected to the connecting portion. The covering portion includes a second support mesh that can be transformed to have a reduced radial profile, and a second gathering member. In preset form, radial profile of the covering portion is not less than radial profile of the plugging portion. The second gathering member is provided at an end of the second support mesh away from the connecting portion. An end of the first gathering member away from the first support mesh and an end of the second gathering member away from the first support mesh are respectively provided with pushing device connection positions, such that the plugging portion has two usage modes: independent usage mode and combined usage mode. In response to independent usage mode, the plugging portion is disconnected from the connecting portion, and a pushing device can be connected with the end of the first gathering member away from the plugging portion. And in response to combined usage mode, the plugging portion is detachably connected to the covering portion through the connecting portion, and the pushing device can be connected with the end of the second gathering member away from the covering portion.

The LAA occluder provided by the above technical solutions differs from the conventional LAA occluder in: an end of the plugging portion close to the connecting portion is provided with the first gathering member; then by structures of the first gathering member and the connecting portion, the plugging portion is detachably connected to the connecting portion. Therefore, the plugging portion can be used in combination with the connecting portion and the covering portion, and can also be used individually. In practice, different combinations can be applied according to different LAA anatomies. The independent use of the plugging portion can avoid affecting tissues near the LAA opening by the covering portion. The combined use of the plugging portion, the connecting portion and the covering portion can cover the residual cavity near the LAA opening, such that no thrombus will occur at the residual cavity. To sum up, the LAA occluder can be used flexibly, and is more adaptive for various LAA anatomies.

Further, the connecting portion includes a threaded connector, a hollow limiting member, and a clamping member. The hollow limiting member has two open ends, and is provided therein with a spherical cavity. One end of the clamping member is rotatably provided in the spherical cavity and matched with the spherical cavity, and the other end is provided with a plugging portion connecting structure. One end of the threaded connector is slidably provided in the hollow limiting member, and the other end is provided with a covering portion connecting structure. The threaded connector is coaxial with the hollow limiting member.

The technical solution further provides specific structures of the connecting portion. Through structures and connection relationships of the threaded connector, the hollow limiting member and the clamping member, relative distance and bending angle between the plugging portion and the covering portion can be changed to further improve the adaptability of the LAA occluder.

Further, the connecting portion includes a first limiting member, a second limiting member, and an elastic member. Cavities opposite to each other are respectively formed in the first limiting member and the second limiting member. The first limiting member is provided in the second limiting member; gaps are provided between the first limiting member and the second limiting member. An end of the first limiting member toward the second limiting member is provided with a first outward-extending bent edge; an end of the second limiting member toward the first limiting member is provided with a second inward-extending bent edge. The first bent edge and the second bent edge radially overlap partially to form an axial limiting structure. The elastic member is provided between the first limiting member and the second limiting member, with two ends respectively connected to the first limiting member and the second limiting member. The first limiting member and the second limiting member may extend or retract axially or bend relatively. Opposite ends of the first limiting member and the second limiting member are respectively provided with connecting structures.

The technical solution further provides another structure of the connecting portion. Through a radial gap and an axial gap between the first limiting member and the second limiting member, relative distance and bending angle between the first limiting member and the second limiting member can be changed. Then relative distance and bending angle between the plugging portion and the covering portion can be changed. This also improves the adaptability of the LAA occluder.

Further, the plugging portion includes a fourth gathering member. The fourth gathering member is provided at an end of the first support mesh away from the connecting portion. The first support mesh includes a plurality of elastic metal wires. The elastic metal wires are interweaved with each other to form a hollow cylindrical structure. Two axial ends of the first support mesh are gathered, and are respectively sealed by the first gathering member and the fourth gathering member. The first gathering member and the fourth gathering member approach each other, such that two axial ends of the plugging portion are recessed. And the first gathering member is provided with a thread structure to match the connecting portion. Or, the plugging portion includes support rods formed by engraving an elastic metal tube. Two axial ends of the plugging portion are gathered, and are respectively sealed by the first gathering member and the fourth gathering member. Or, only an end of the plugging portion close to the connecting portion is gathered by the first gathering member. And the first gathering member is provided with a thread structure to match the connecting portion. Or, the plugging portion is a cylinder having two axial ends with basically same radial profiles.

Further, the covering portion includes a third gathering member. The third gathering member is provided at an end of the second support mesh close to the connecting portion. The connecting portion is detachably connected to the covering portion through the third gathering member. The second support mesh includes a plurality of elastic metal wires. The elastic metal wires are interweaved with each other to form a hollow flat structure. Two axial ends of the second support mesh are gathered, and are respectively sealed by the second gathering member and the third gathering member. The second gathering member and the third gathering member are coaxial with the covering portion. A center of an end of the covering portion towards the connecting portion is convex. And/or, polymer membranes are respectively provided in the plugging portion and the covering portion. The technical solution further provides a specific structure of the second support mesh, an internal structure of the plugging portion and an internal structure of the covering portion. By respectively providing the polymer membranes in the plugging portion and the covering portion, blocking ability of blood flow is effectively promoted. In addition, in practice, LAA anatomies vary due to individual differences, and thus various size combinations of the covering portion and the plugging portion. By detachable connection between the covering portion and the connecting portion, various size combinations of the covering portion and the plugging portion are realized. This further improves the adaptability of the LAA occluder to various LAA anatomies.

Further, an end of the clamping member away from the hollow limiting member is provided with an external thread or an internal thread to form the plugging portion connecting structure. And the first gathering member is matched with the plugging portion connecting structure. And/or, an end of the threaded connector away from the hollow limiting member is provided with an external thread or an internal thread to form the covering portion connecting structure.

Further, the anchoring members each includes a free end and a fixed end. The fixed end is fixedly connected to the plugging portion, while the free end extends outward. The plurality of anchoring members surround the outer peripheral surface of the plugging portion. Each of the anchoring members has a length of 1-4 mm. The plurality of anchoring members are respectively located at edges of 1-3 cross sections of the plugging portion. Each cross sections' edge is provided with 4-10 anchoring members. The plurality of anchoring members located at edges of different cross section are misaligned along a radial direction of the plugging portion.

Further, a resistance member is provided at a junction between the first gathering member and the connecting portion to increase connection strength of the junction. The resistance member includes a plurality of first sawtooth-like structures and a plurality of second sawtooth-like structures. The first sawtooth-like structures are arranged at an end of the first gathering member toward the connecting portion. The second sawtooth-like structures are arranged at an end of the connecting portion toward the first gathering member. In a connected state, the first sawtooth-like structures are locked with the second sawtooth-like structures. Or, the resistance member includes a resistance washer. The resistance washer is annular, and made of biocompatible flexible material such as polyester membrane, polytetrafluoroethylene (PTFE) membrane, etc. Two axial ends of the resistance washer each are provided with a plurality of protrusions. And in the connected state, the resistance washer is compressed by the first gathering member and the connecting portion.

Further, the resistance member includes a first resistance washer and a second resistance washer. An axial end of the first resistance washer is connected to the first gathering member, and the other end of the first resistance washer is zigzag. The second resistance washer is slidably sleeved to the connecting portion. An end of the second resistance washer away from the plugging portion is provided with a spring, and the other end of the second resistance washer is zigzag. And in the connected state, the first resistance washer presses the second resistance washer along the axial direction. The spring is compressed axially under pressure of the second resistance washer. And the zigzag end of the first resistance washer is engaged with the zigzag end of the second resistance washer. Or, the resistance member includes an internal threaded tube. In the connected state, the internal threaded tube is sleeved to the first gathering member and the connecting portion. And external threads matched with the internal threaded tube are respectively provided on a surface of the first gathering member and a surface of the connecting portion.

The technical solution further provides the resistance member. With various types of the resistance member, the connection strength between the plugging portion and the connecting portion is improved simply and reliably. When the plugging portion and the connecting portion are delivered by the pushing device to the LAA opening, the connection between the plugging portion and the connecting portion is not affected even by large external force, such as the force produced when the pushing device is separated from the pushing device connection position of the covering portion.

A method of application for an LAA occluder includes: detecting an LAA anatomy.

In a case where an implantation position of the plugging portion is apart from an LAA opening, and an obvious residual cavity near an LAA opening cannot be sealed by the plugging portion only, the method of application includes following steps.

step 1: sequentially connecting the plugging portion, the connecting portion and the covering portion, connecting an end of the covering portion away from the connecting portion with the pushing device, stretching the covering portion and the plugging portion to transform into linear shape, and allowing the pushing device to push the LAA occluder to a human body through a delivery sheath;

step 2: pushing, at the implantation position, the plugging portion out of the delivery sheath, where the support mesh of the plugging portion away from the connecting portion expands gradually to form a small plane for pre-targeting; a remaining part of the first support mesh expands sequentially, such that the plugging portion gradually attaches to LAA tissues; and the anchoring members expand at the same time to grasp LAA tissues; and step 3: sequentially pushing the connecting portion and the covering portion out of the delivery sheath, where the covering portion expands to cover the LAA opening.

The technical solution provides the method of application for the LAA occluder. On the one hand, the method effectively occludes the LAA by combination of the plugging portion, the connecting portion and the covering portion, in the case where the implantation position of the plugging portion is apart from the LAA opening, and the obvious residual cavity near the LAA opening cannot be sealed. On the other hand, when the LAA occluder is pushed out, the support mesh of the plugging portion away from the connecting portion expands gradually to form a small plane for pre-targeting. The plugging portion expands in the LAA from the relatively flat front end, which effectively prevents potential damages to LAA tissues by the device. The first support mesh and the anchoring members that gradually restore to preset shapes attach to inner surfaces of the LAA, which effectively grasps LAA tissues and prevents damages.

Further, when an implantation position of the plugging portion is close to the LAA opening, and the plugging portion may basically seal the LAA opening without obvious residual cavity, the method of application includes the following steps.

step 1: connecting the plugging portion to the pushing device through the first gathering member, stretching the covering portion to transform into linear shape, and allowing the pushing device to push the LAA occluder to a human body through the delivery sheath;

step 2: gradually pushing, at the implantation position, the plugging portion out of the delivery sheath, where the support mesh of the plugging portion away from the connecting portion expands gradually to form a small plane for pre-targeting; a remaining part of the support mesh expands sequentially, such that the plugging portion gradually attaches to LAA tissues; and the anchoring members expand at the same time to grasp LAA tissues; and step 3: operating the pushing device, such that the pushing device is separated from the plugging portion, and the plugging portion is used individually to seal the LAA opening.

The technical solution further provides the method of application for the LAA occluder. On the one hand, the method effectively occludes the LAA by independent use of the plugging portion and the connecting portion, in the case where the implantation position of the plugging portion is close to the LAA opening, and the LAA opening can be sealed basically by the plugging portion. On the other hand, when the LAA occluder is pushed out, the support mesh of the plugging portion away from the connecting portion expands gradually to form a small plane for pre-targeting. The plugging portion expands in the LAA from the relatively flat front end, which effectively prevents potential damages to LAA tissues by the device. The first support mesh and the anchoring members that gradually restore to preset shapes attach to inner surfaces of the LAA, which effectively grasps LAA tissues and prevents damages.

The present disclosure at least achieves one of the following technical effects:

1. The plugging portion is detachably connected to the connecting portion, such that the plugging portion can be used in combination with the connecting portion and the covering portion, and can also be used individually. Therefore, the LAA occluder may be used flexibly, and is more adaptive to various LAA anatomies.

2. Through the third gathering member that functions as connection hub between the covering portion and the connecting portion, the covering portion is detachably connected to the connecting portion. Such that, various size combinations of the covering portion and the plugging portion are realized. This further improves the adaptability of the LAA occluder to various LAA anatomies.

3. Through structures and connection relationships of the threaded connector, the hollow limiting member and the clamping member, relative distance and bending angle between the plugging portion and the covering portion can be changed to further improve the adaptability of the LAA occluder.

4. Through a radial gap and an axial gap between the first limiting member and the second limiting member, relative distance and bending angle between the first limiting member and the second limiting member can be changed. Thus, relative distance and bending angle between the plugging portion and the covering portion can be changed. This also improves the adaptability of the LAA occluder.

5. With combined use of the plugging portion, the connecting portion and the covering portion or independent use of the plugging portion, the method effectively occludes the LAA, considering the case where the implantation position of the plugging portion is apart from an LAA opening, and the obvious residual cavity near the LAA opening cannot be sealed. In addition, when the LAA occluder is pushed out, the support mesh of the plugging portion away from the connecting portion expands gradually to form a small plane for pre-targeting. The plugging portion expands in the LAA from the relatively flat front end, which effectively prevents potential damages to LAA tissues by the device. The first support mesh and the anchoring members that gradually restore to preset shapes attach to inner surfaces of the LAA, which effectively grasps LAA tissues and prevents damages.
6. With the connecting structure between the plugging portion and the covering portion, the plugging portion and the covering portion may present the flexibility with different axis. This is more adaptive for different LAA anatomies.
7. The plugging portion can be used in combination with the covering portion, or the plugging portion can be used individually. In clinical application, according to the actual LAA anatomies, the independent use of the plugging portion or the combined use of the plugging portion and the covering portion can be selected.
8. Sizes of the plugging portion and the covering portion can be selected more flexibly. This expands the application scope and shortens the time of operation.
9. With the resistance member, the connection strength between the plugging portion and the connecting portion in the connected state is effectively increased.

BRIEF DESCRIPTION OF THE DRAWINGS

The present disclosure is described in further detail below with reference to the drawings and specific implementations.

REFERENCE NUMERALS

Figure 1:
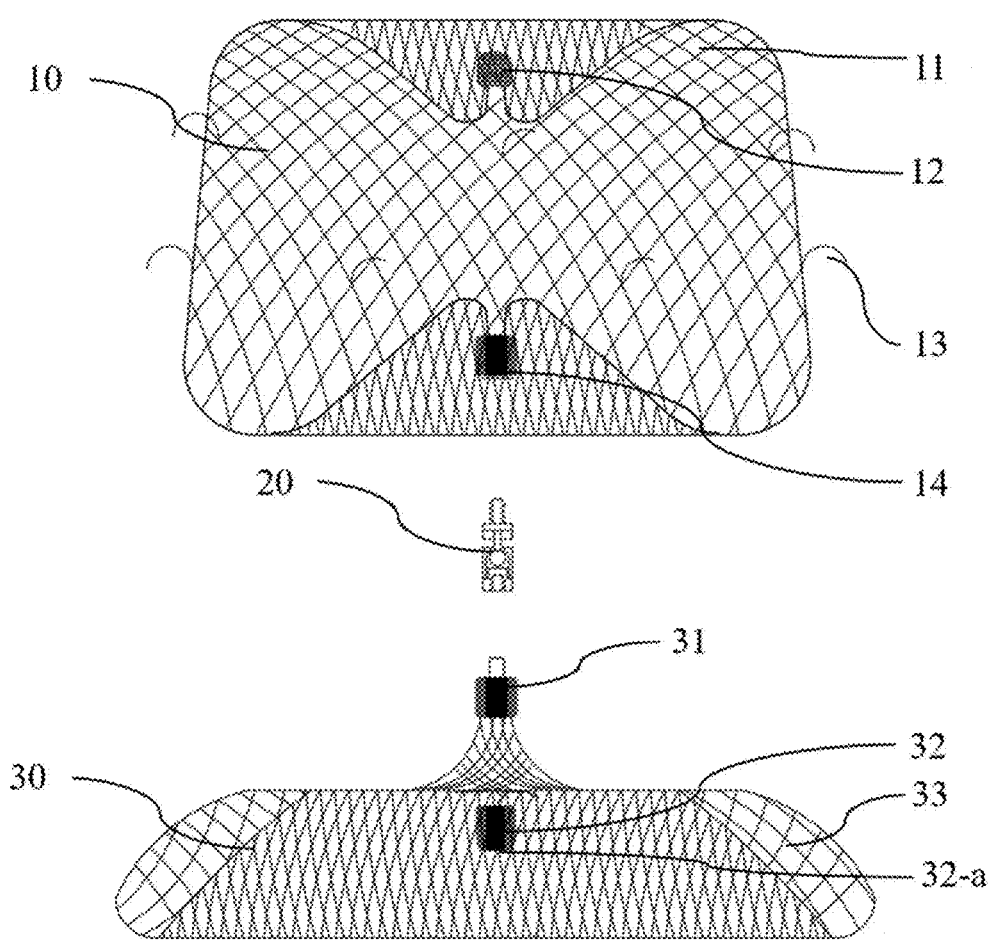
FIG. 1 is a schematic structural view according to an embodiment of the present disclosure.

10: plugging portion, 11: first support mesh, 12: fourth gathering member, 13: anchoring member, and 14: first gathering member;

20: connecting portion, 21: threaded connector, 21-a: covering portion connecting structure, 22: hollow limiting member, 23: clamping member, 23-a: plugging portion connecting structure, 24: first limiting member, 24-*a*: first bent edge, 25: second limiting member, 25-*a*: second bent edge, 26: elastic member, 27: cavity, and 28: connecting structure;

30: covering portion, 31: third gathering member, 32: second gathering member, 32-*a*: pushing device connection position, and 33: second support mesh;

40: LAA, 41: LAA opening, and 42: LAA sac;

50: resistance member, 51: first sawtooth-like structure, 52: second sawtooth-like structure, 53: resistance washer, 54: protrusion, 55: first resistance washer, 56: second resistance washer, 57: spring, and 58: internal threaded tube; and 60: pushing device, and 61: delivery sheath.

DETAILED DESCRIPTION OF THE EMBODIMENTS

In order to explain the embodiments of the present disclosure or the technical solutions in the prior art more clearly, the specific implementations of the present disclosure will be described below with reference to the drawings. Apparently, the drawings in the following description show merely some embodiments of the present disclosure, and other drawings and other implementations may be derived from these drawings by those of ordinary skill in the art without creative efforts.

In order to keep the drawings concise, the drawings only show components related to the present disclosure, but it does not necessarily mean that these components represent the actual structure of the product. Further, for the purpose of better understanding, only one of components having the same structure or function is schematically shown or marked in some drawings. In the description of the present disclosure, "one" not only means "only one", but also means "more than one".

It should also be further understood that the term "and/or" used in this specification of the utility model and the appended claims refers to one or any or all possible combinations of a plurality of associated items that are listed, and includes these combinations.

In the description of the present disclosure, it should be noted that, unless otherwise clearly specified, meanings of terms "provided", "connected with", and "connected to" should be understood in a board sense. For example, the connection may be a fixed connection, a removable connection, or an integral connection; may be a mechanical connection or an electrical connection; may be a direct connection or an indirect connection by using an intermediate medium; or may be intercommunication between two components. A person of ordinary skill in the art may understand specific meanings of the foregoing terms in the present disclosure based on a specific situation.

In addition, in the description of the present disclosure, the terms such as "first" and "second" are used only for distinguishing, rather than to indicate or imply relative importance.

In order to explain the embodiments of the present disclosure or the technical solutions in the prior art more clearly, the specific implementations of the present disclosure will be described below with reference to the drawings. Apparently, the drawings in the following description show merely some embodiments of the present disclosure, and other drawings and other implementations may be derived from these drawings by those of ordinary skill in the art without creative efforts.

Embodiment 1

Figure 7:
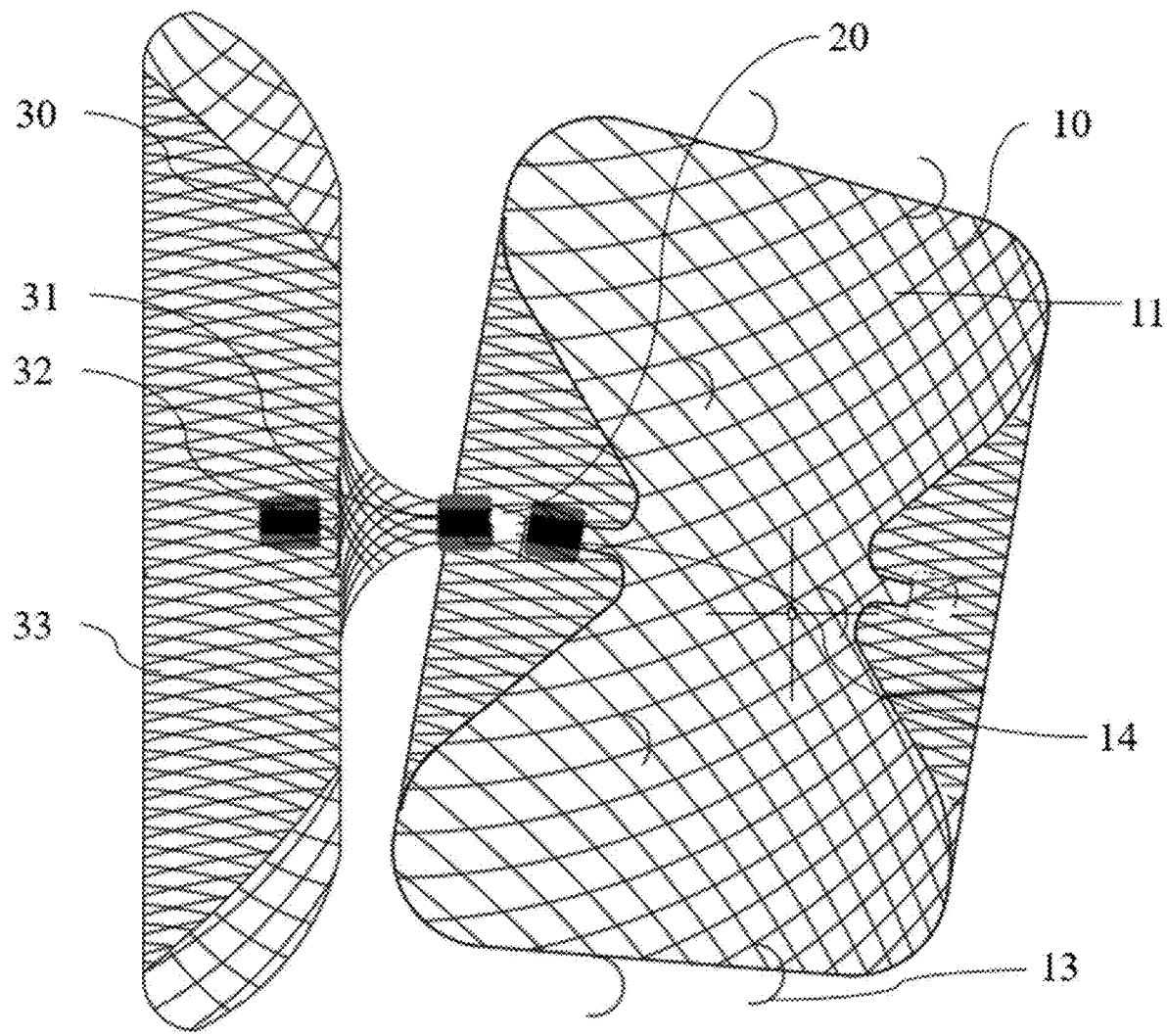
FIG. 7 is a schematic structural view in a use state according to an embodiment of the present disclosure.

As shown in FIG. 1 and FIG. 7, an LAA occluder includes plugging portion 10, connecting portion 20, and covering portion 30 that are connected axially.

Figure 2:
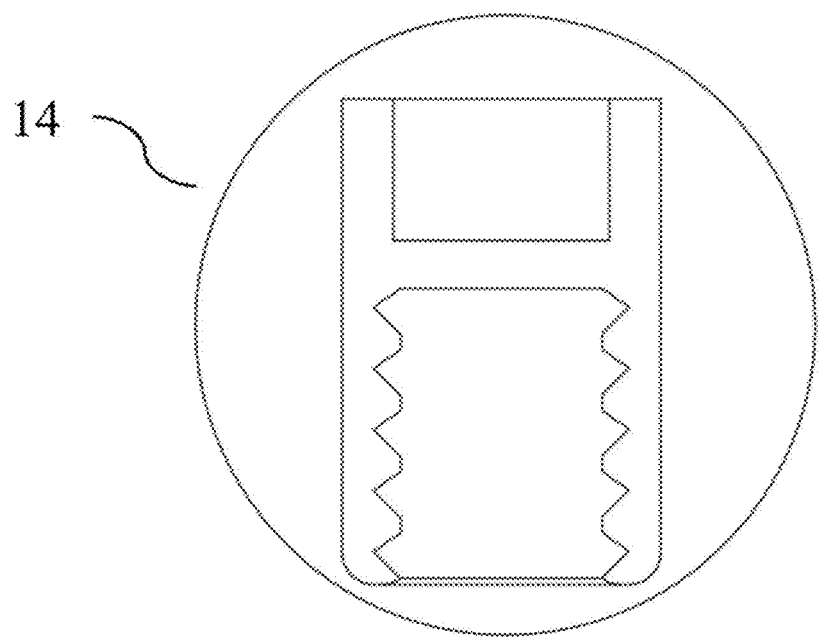
FIG. 2 is a schematic structural view of a first gathering member according to an embodiment of the present disclosure.

Specifically, the plugging portion 10 includes first support mesh 11 that can be transformed to have a reduced radial profile, and first gathering member 14. A plurality of anchoring members 13 for grasping LAA tissues are arranged on outer peripheral surface of the first support mesh 11. The first gathering member 14 is provided at an end of the first support mesh 11 close to the connecting portion 20. The first gathering member 14 is detachably connected to the connecting portion 20, such that the plugging portion 10 can be individually placed in an LAA. In a preferred embodiment, as shown in FIG. 2, one end of the first gathering member 14 is provided with a cavity structure for collecting the first support mesh 11, and the other end is provided with an internal thread structure that can be detachably connected to the connecting portion 20.

Further, the covering portion 30 includes second support mesh 33 that can be transformed to have a reduced radial profile, and second gathering member 32. In preset form, radial profile of the covering portion 30 is not less than radial profile of the plugging portion 10. The second gathering member 32 is provided at an end of the second support mesh 33 away from the connecting portion 20. An end of the second gathering member 32 away from the connecting portion 20 is provided with pushing device connection position 32-*a*. It is to be noted that the pushing device connection position 32-*a* refers to a connection position between the device and pushing device 60, and its specific connecting structure may be threaded connection, clearance-fit connection or connection in other forms.

Figure 4:
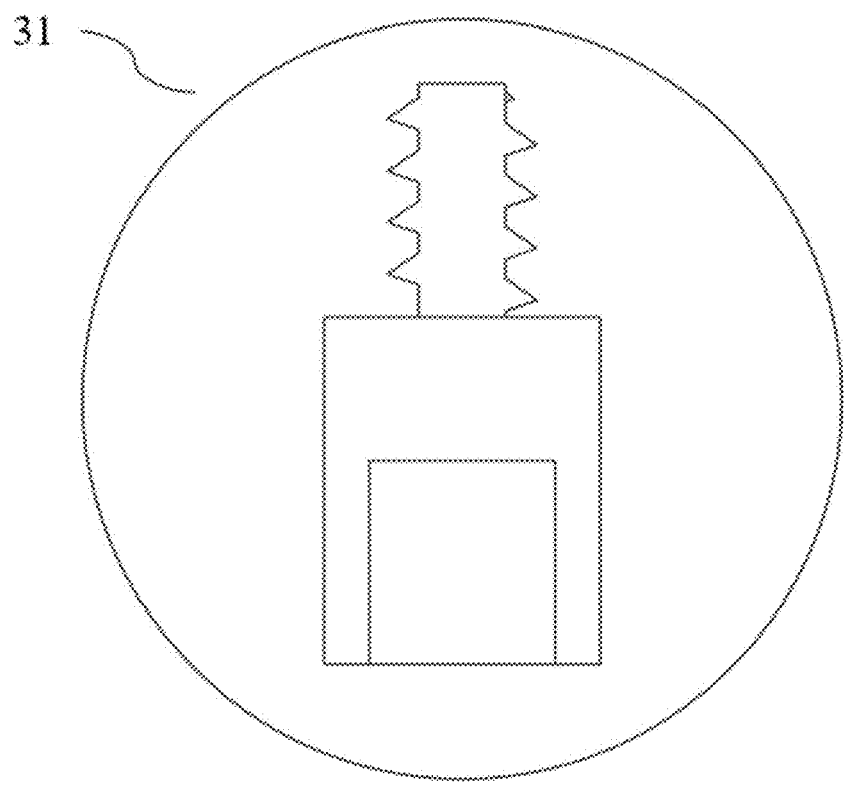
FIG. 4 is a schematic structural view of a third gathering member according to an embodiment of the present disclosure.

Further preferably, as shown in FIG. 4, the covering portion 30 includes third gathering member 31. The third gathering member 31 is provided at an end of the second support mesh 33 close to the connecting portion 20. The connecting portion 20 can be detachably connected to the covering portion 30 through the third gathering member 31.

In practice, the plugging portion 10 may be used individually, and may also be used in combination with the connecting portion 20 and the covering portion 30. Specifically, in response to independent use of the plugging portion, the plugging portion 10 is detachably connected to the pushing device 60 through the first gathering member 14, namely a side of the first gathering member 14 away from the first support mesh 11 is provided with a pushing device connection position. In response to combined use of the plugging portion, the plugging portion 10 is detachably connected to the connecting portion 20. An end of the connecting portion 20 away from the plugging portion 10 is detachably connected to the covering portion 30 through the third gathering member 31. It is to be noted that the pushing device connection position at the end of the connecting portion 20 away from the plugging portion 10 is provided with a connecting structure matched with the pushing device 60.

Further, elastic metal wires of the second support mesh 33 are collected through the second gathering member 32 and the third gathering member 31, such that the covering 30 forms an enclosed structure. Specifically, a tip of the connecting portion 20 is provided with an external thread structure. A nut structure is provided in the third gathering member 31. Such that the third gathering member 31 can be detachably connected to the connecting portion 20. In a preferred embodiment, polymer membranes are respectively provided in the plugging portion 10 and the covering portion 30.

Further preferably, the anchoring members 13 each includes a free end and a fixed end. The fixed end is fixedly connected to the plugging portion 10, while the free end extends outward. The plurality of anchoring members 13 surround the outer peripheral surface of the plugging portion 10. The anchoring members 13 each has a length of 1-4 mm. The plurality of anchoring members 13 are respectively located at edges of 1-3 cross sections of the plugging portion 10. Each cross sections' edge is provided with 4-10 anchoring members 13. When the anchoring members 13 are not located on a same cross section, the anchoring members 13 are misaligned along a radial direction of the plugging portion 10.

In actual application, different usage modes and sizes of the LAA occluder can be selected based on different LAA anatomies.

Figure 10:
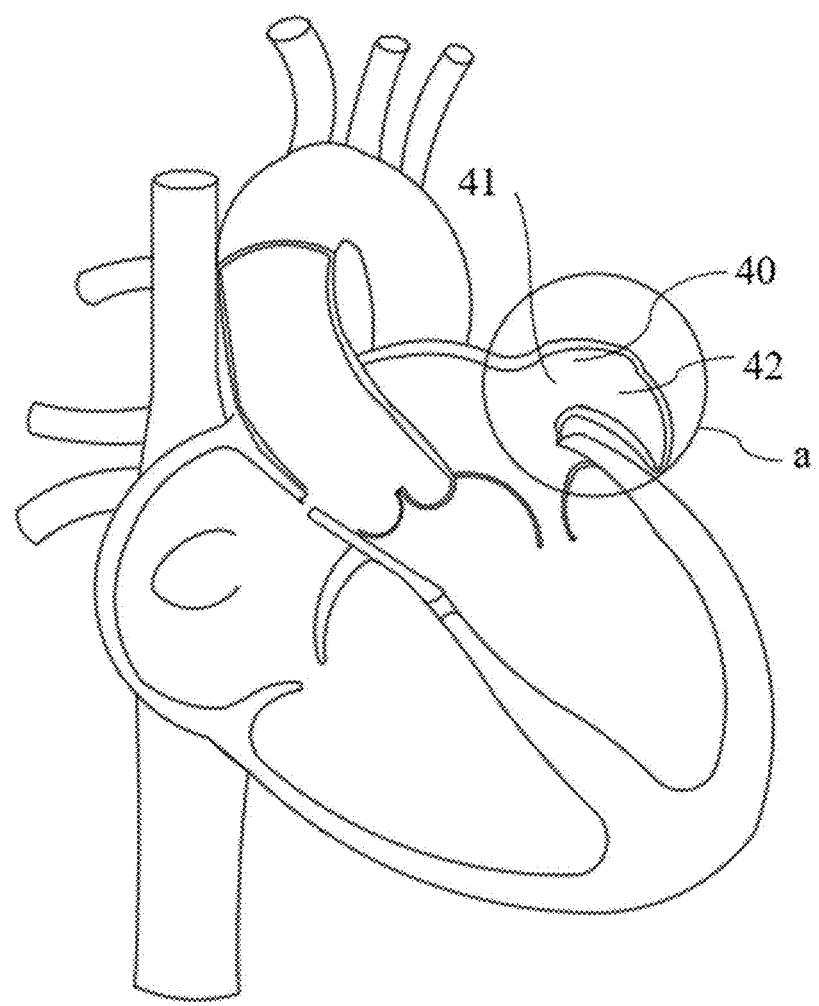
FIG. 10 is a schematic view inside a heart.
Figure 12:
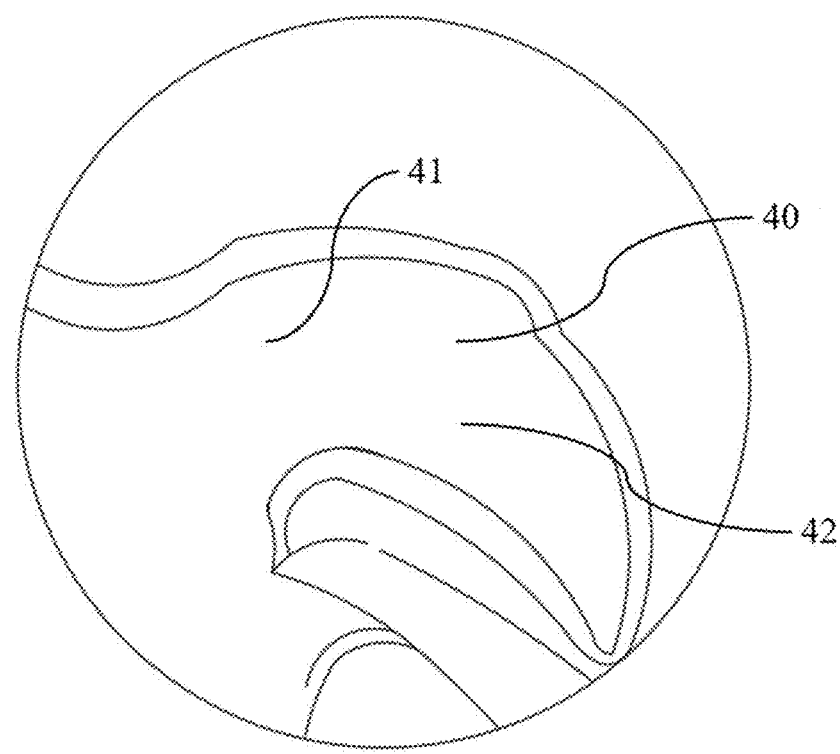
FIG. 12 is a partial enlarged view of a region a in FIG. 10.

Typically, LAA 40 includes LAA opening 41 and LAA sac 42. The LAA opening 41 communicates with an LA. The LAA 40 varies from person to person, and its anatomical structure can be approximately classified as follows:

First type: As shown in FIG. 10 and FIG. 12, a radial profile of the LAA opening 41 is approximately same as a radial profile of a segment of the adjacent LAA sac 42.

Figure 14:
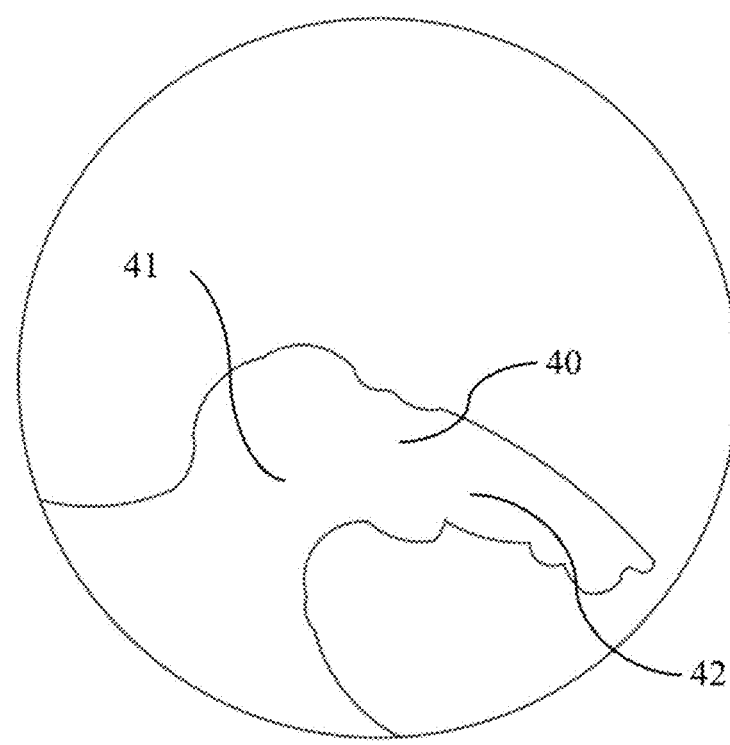
FIG. 14 is a partial schematic view of an LAA anatomy.

Second type: As shown in FIG. 14, the LAA opening 41 has a small radial profile. The LAA sac 42 adjacent to the LAA opening 41 has an increased radial profile over the LAA opening 41 and has a large turning angle.

Figure 16:
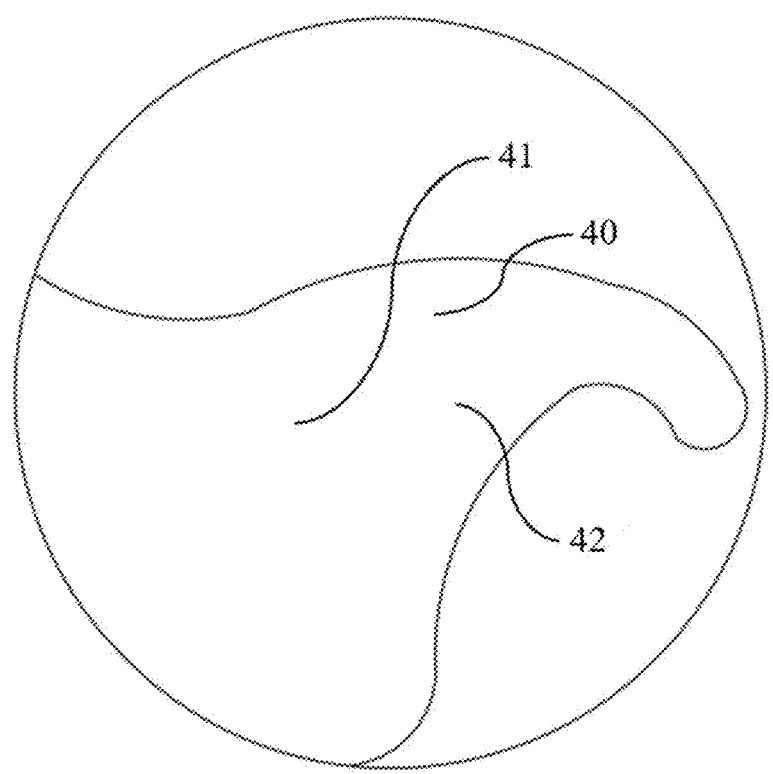
FIG. 16 is a partial schematic view of an LAA anatomy.

Third type: As shown in FIG. 16, the LAA opening 41 has a large radial profile. The LAA sac 42 has a smaller radial profile than the LAA opening 41.

Figure 18:
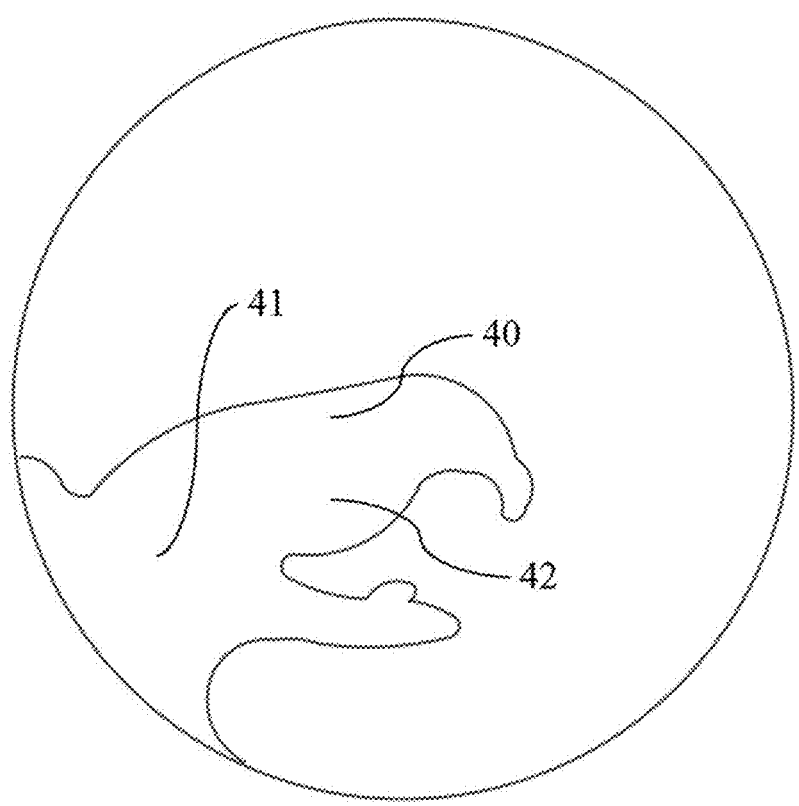
FIG. 18 is a partial schematic view of an LAA anatomy.

Fourth type: As shown in FIG. 18, the LAA sac 42 includes more than one leaflet.

Figure 11:
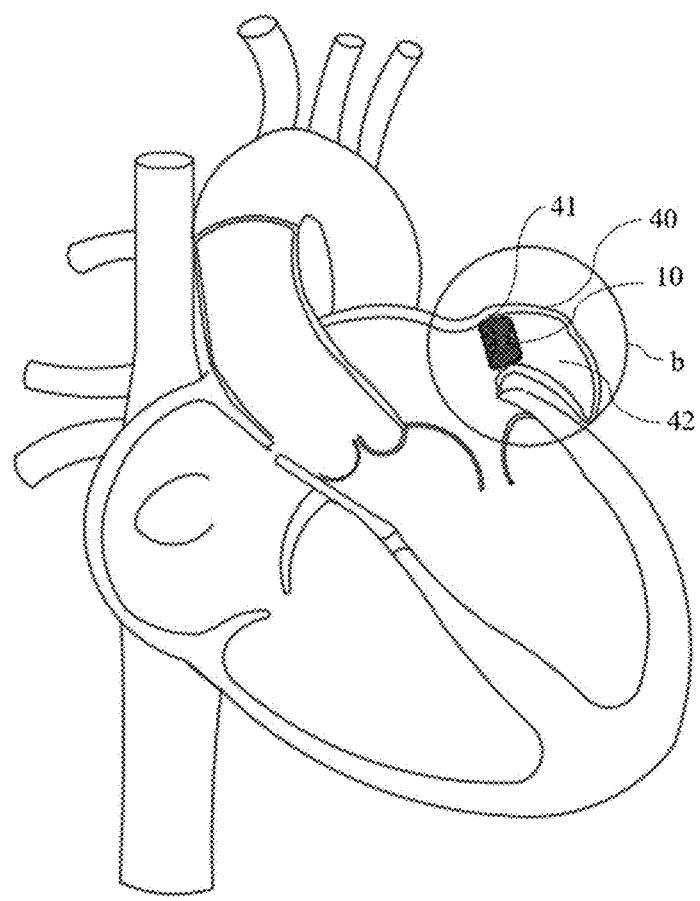
FIG. 11 illustrates an effect of an LAA occluder in an LAA anatomy in FIG. 10.
Figure 13:
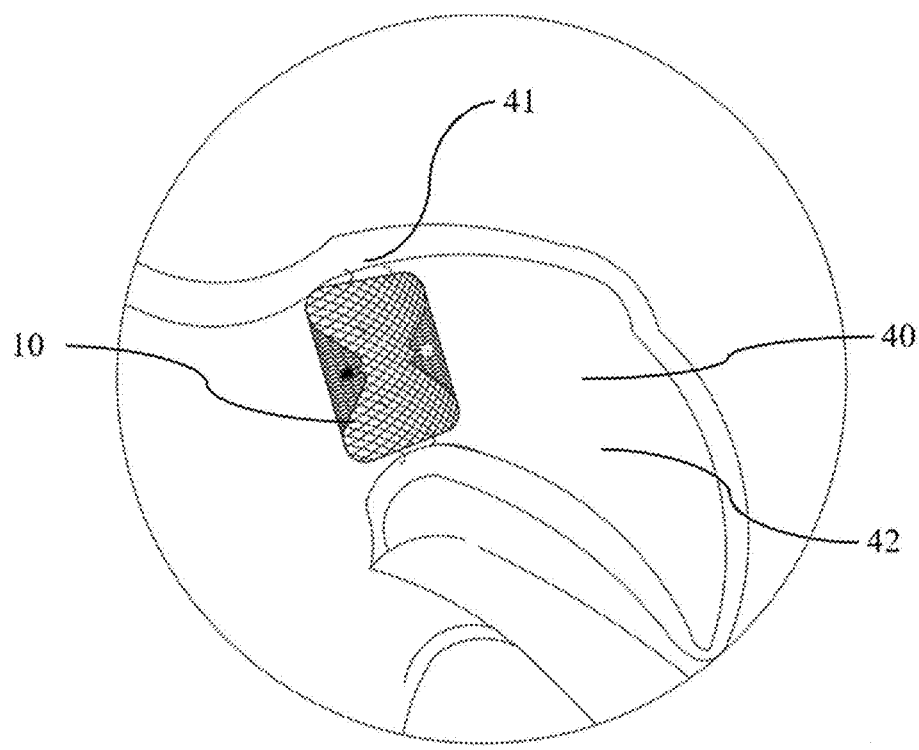
FIG. 13 is a partial enlarged view of a region b in FIG. 11.

For the first type of LAA anatomy, as shown in FIG. 11 and FIG. 13, the implantation position of the plugging portion 10 is close to the LAA opening 41, and the LAA opening 41 may be basically sealed by the plugging portion 10 without a residual cavity. In this case, the plugging portion 10 may be used individually. Because of no residual cavity at the LAA opening 41, a channel between the LAA and the LA is occluded.

For the second, third and fourth type of LAA anatomy, the covering portion 30, the connecting portion 20 and the plugging portion 10 are combined for occlusion.

Figure 15:
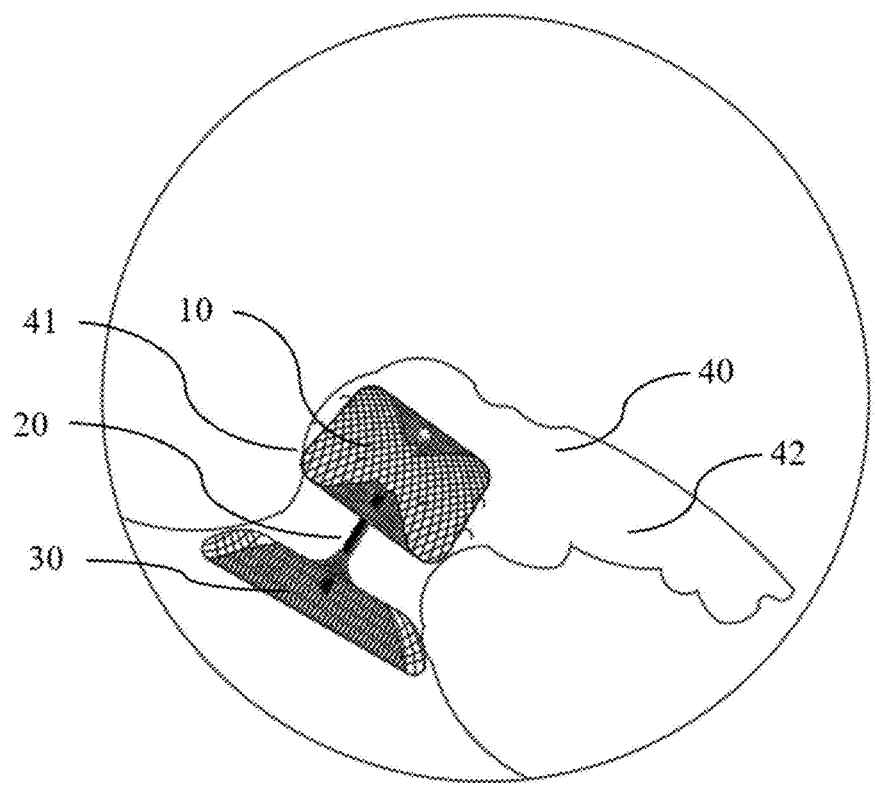
FIG. 15 illustrates an effect of an LAA occluder in an LAA anatomy in FIG. 14.

In a preferred embodiment, as shown in FIG. 7, double layers of the support mesh on a main body of the covering portion 30 are close to each other in the axial direction. The whole covering portion 30 is approximately truncated-cone-shaped, with a certain upward protruding radian in a circumferential direction, and a distal end approximately forming a small hollow truncated-cone-shaped space. The truncated cone has a height of 3-6 mm. In addition, the main body of the covering portion 30 is approximately a plane. When the LAA anatomy is shallow, the covering portion 30 is almost located out of the LAA, and thus the plane structure can be used. The above two structures are more applicable to the second type of LAA anatomy shown in FIG. 14, and the occlusion effect is shown in FIG. 15.

Figure 17:
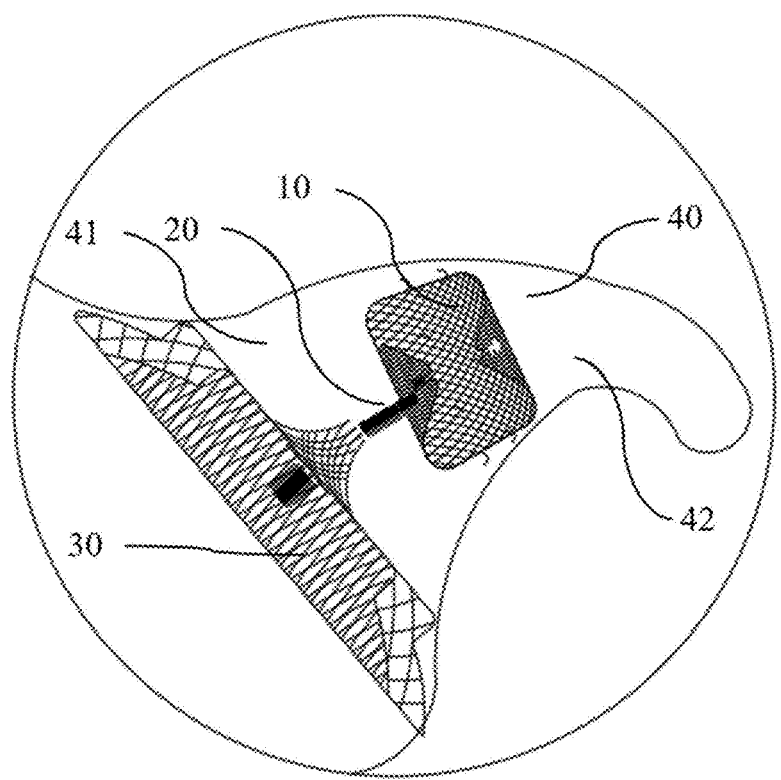
FIG. 17 illustrates an effect of an LAA occluder in an LAA anatomy in FIG. 16.
Figure 19:
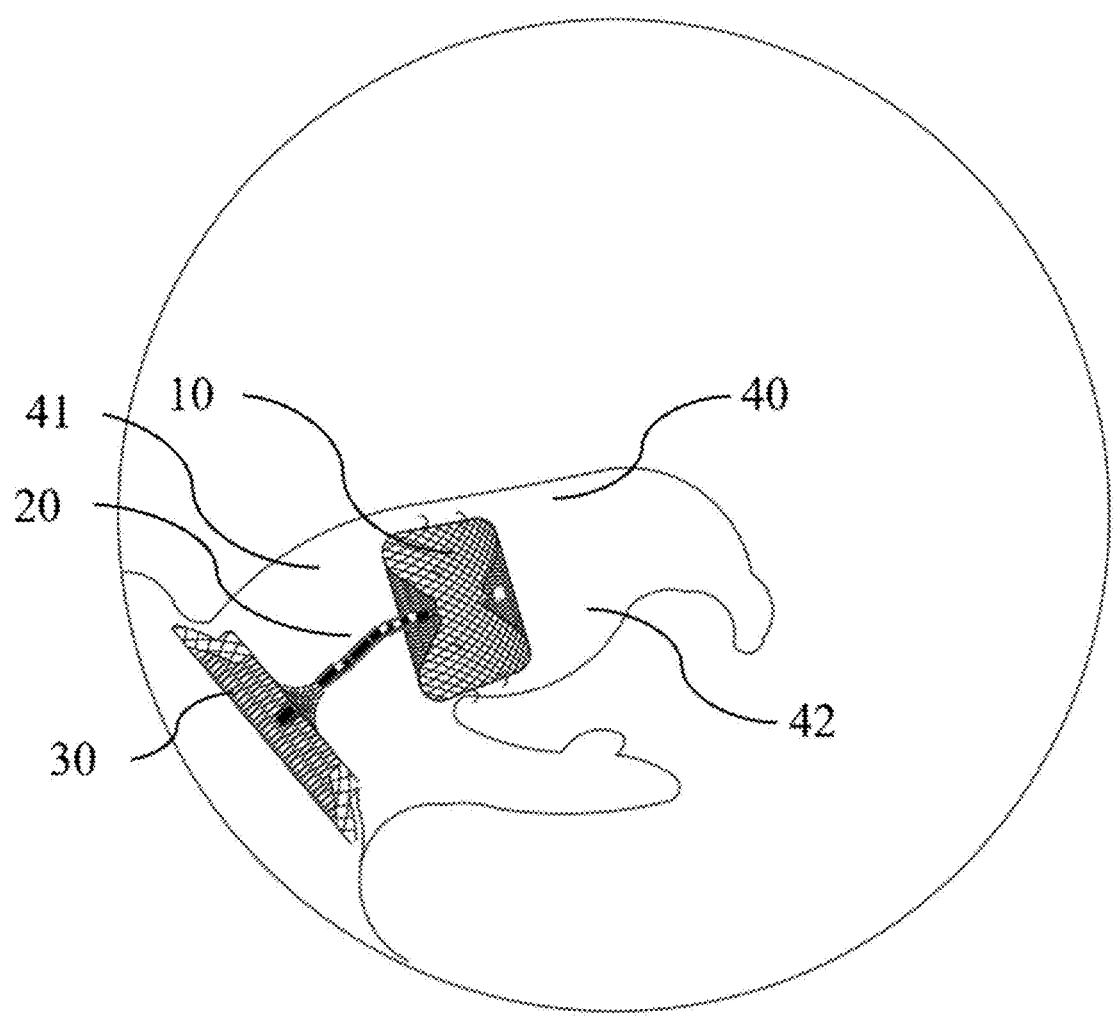
FIG. 19 illustrates an effect of an LAA occluder in an LAA anatomy in FIG. 18.
Figure 20:
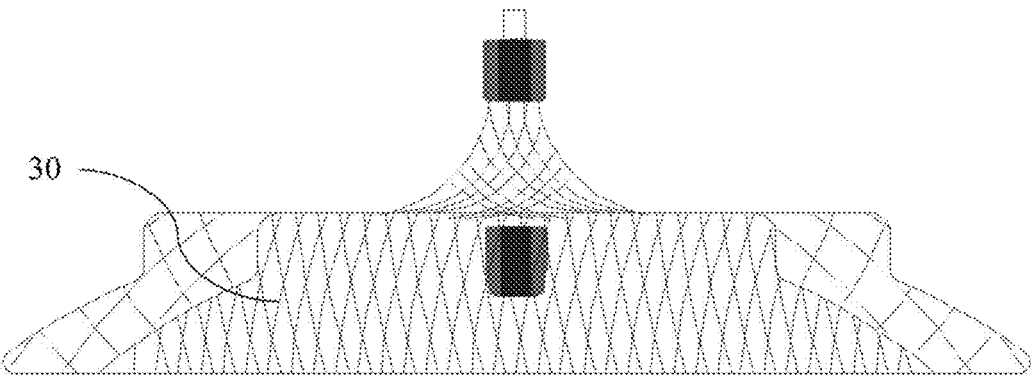
FIG. 20 is a schematic structural view of a covering portion according to an embodiment of the present disclosure.

In a preferred embodiment, as shown in FIG. 20, the covering portion 30 is axially provided with an annular step. This increases an edge with a larger radial profile for the covering portion 30, and realizes dual occlusion to the LAA opening 41, thereby ensuring the occlusion effect. As shown in FIG. 15, FIG. 17 and FIG. 19, the combined structure for the covering portion 30 with the annular step, the connecting portion 20 and the plugging portion 10 is applicable to the third and fourth types of LAA anatomy. The covering portion 30 attaches to the LAA opening 41 more easily to occlude the LAA.

Embodiment 2

The LAA occluder in the embodiment differs from Embodiment 1 mainly in a specific structure of the connecting portion 20. Contents same as above will not be repeated herein.

Figure 3:
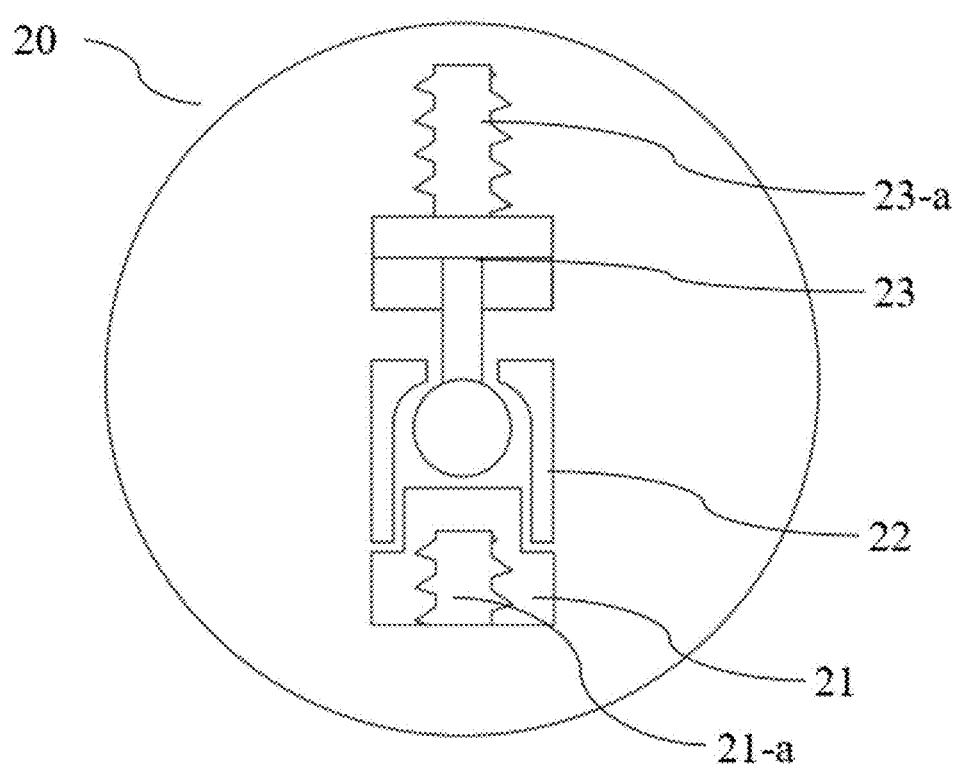
FIG. 3 is a schematic structural view of a connecting portion according to an embodiment of the present disclosure.
Figure 8:
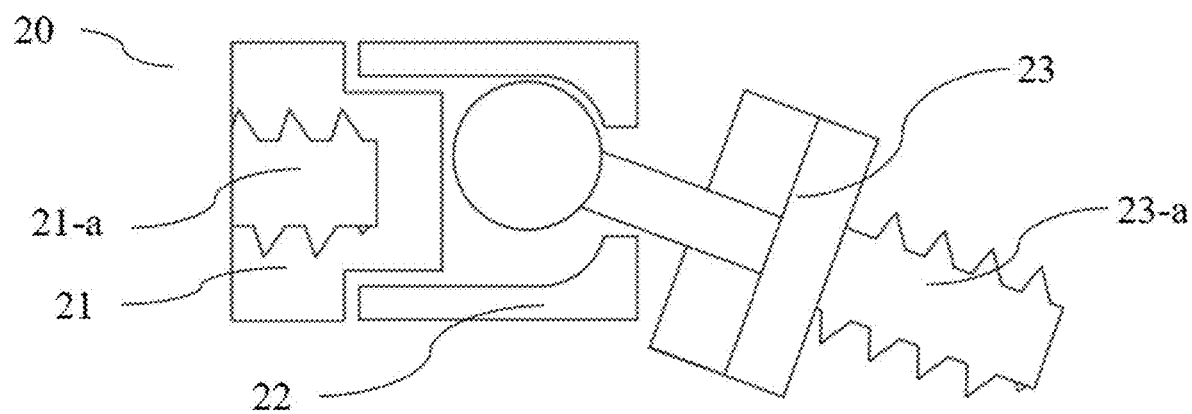
FIG. 8 is a schematic structural view of a connecting portion in a use state according to an embodiment of the present disclosure.

Specifically, as shown in FIG. 3 and FIG. 8, the connecting portion 20 includes threaded connector 21, hollow limiting member 22, and clamping member 23. The hollow limiting member 22 has two open ends, and is provided therein with a spherical cavity. One end of the clamping member 23 is rotatably provided in the spherical cavity and matched with the spherical cavity, and the other end is provided with a plugging portion connecting structure 23-$a$. One end of the threaded connector 21 is slidably provided in the hollow limiting member 22 and coaxial with the hollow limiting member, and the other end is provided with covering portion connecting structure 21-$a$. It is to be noted that the plugging portion connecting structure 23-$a$ and the covering portion connecting structure 21-$a$ may use any one of an internal thread structure, an external thread structure and a clearance-fit connecting structure.

Further preferably, the plugging portion 10 includes fourth gathering member 12. The fourth gathering member 12 is provided at an end of the first support mesh 11 away from the connecting portion 20. The first support mesh 11 includes a plurality of elastic metal wires. The elastic metal wires are interweaved with each other to form a hollow cylindrical structure. Two axial ends of the plugging portion are gathered, and are respectively sealed by the first gathering member 14 and the fourth gathering member 12. The first gathering member 14 and the fourth gathering member 12 approach each other, such that the two axial ends of the plugging portion 10 are recessed. The first gathering member 14 is provided with a thread structure to match the connecting portion 20.

Preferably, a recessed range of a plane where the first gathering member 14 is located is greater than a recessed range of a plane where the fourth gathering member 12 is located.

Figure 6:
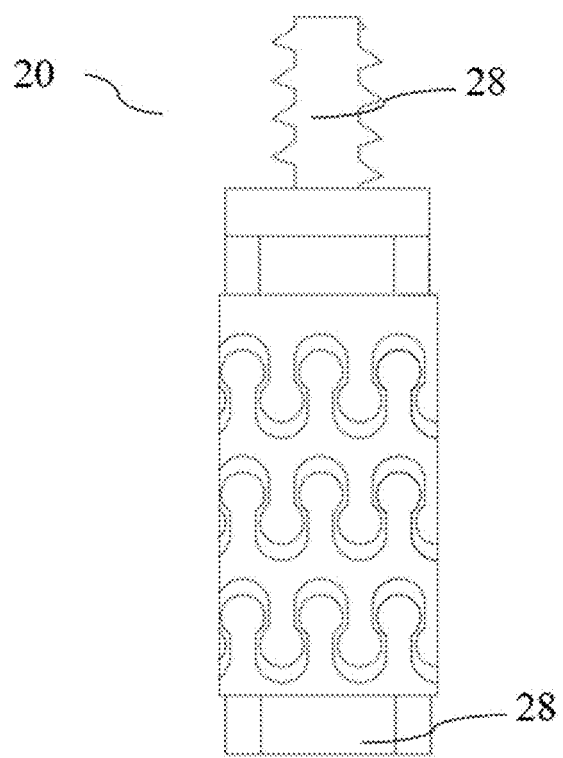
FIG. 6 is a schematic structural view of a connecting portion according to an embodiment of the present disclosure.
Figure 9:
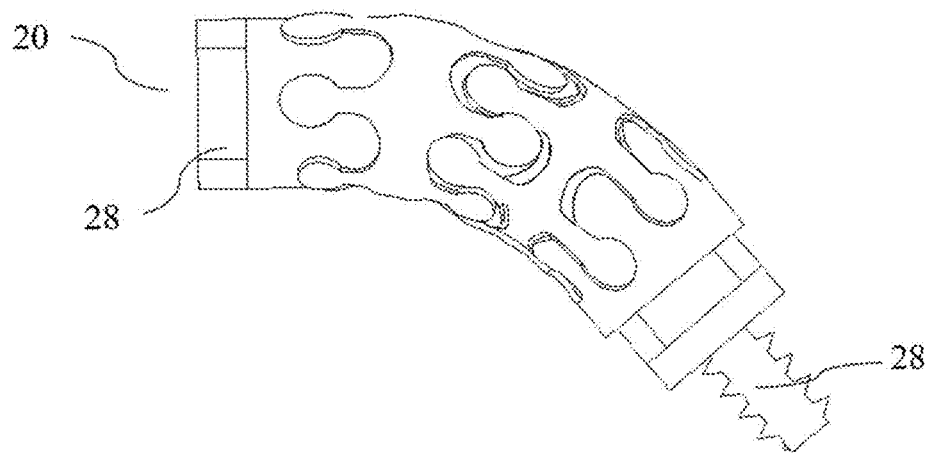
FIG. 9 is a schematic structural view of a connecting portion in a use state according to an embodiment of the present disclosure.

In another preferred embodiment, as shown in FIG. 6 and FIG. 9, a middle of the connecting portion 20 uses a hollow tube made of an elastic metal tube material. The hollow tube is engraved to form connecting units engaged with each other. A gap is provided between adjacent connecting units, thereby forming a certain bending space. The tubular member can be elongated or shortened, such that the gap between the connecting units can increase or decrease to adjust a length and a bending range of a main body portion. Connecting structures 28 are respectively arranged at two ends of the connecting portion 20. The connecting structure 28 may use any one of an internal thread structure, an external thread structure and a clearance-fit connecting structure.

In another preferred embodiment, the plugging portion 10 includes support rods formed by engraving an elastic metal tube. Two axial ends of the plugging portion are gathered, and are respectively sealed by the first gathering member 14 and the fourth gathering member 12. Or, only an end of the plugging portion 10 close to the connecting portion 20 is gathered by the first gathering member 14, and the first gathering member 14 is provided with a thread structure to match the connecting portion 20.

In another preferred embodiment, the plugging portion 10 is a cylinder having two axial ends with basically same radial profiles.

Further preferably, the second support mesh 33 includes a plurality of elastic metal wires. The elastic metal wires are interweaved with each other to form a hollow flat structure. Two axial ends of the second support mesh 33 are gathered, and are respectively sealed and fixed by the second gathering member 32 and the third gathering member 31. The second gathering member 32 and the third gathering member 31 are coaxial with the covering portion 30. A center of an end of the covering portion 30 towards the connecting portion 20 is convex.

In other words, the second support mesh 33 may be an approximately sheet-like structure, and has a certain radian in a radial direction. A position closer to a center has a smaller radius of curvature, such that the covering portion 30 tends to approach the second gathering member 32 from an edge to the center. When the LAA occluder is implanted into the LAA, it is better to keep a tension between the covering portion 30 and the plugging portion 10, such that the covering portion 30 tightly attaches to the LAA opening 41, and does not move under an impact of a blood flow to cause peri-device leak (PDL). With the radian, the center of the covering portion 30 is closer to the plugging portion 10. Through the tension between the covering portion and the plugging portion, the covering portion 30 attaches to the LAA opening 41 more easily to prevent the PDL.

Embodiment 3

The LAA occluder in the embodiment is a parallel solution to the structural solution of the connecting portion 20 in Embodiment 2. Contents same as above will not be repeated herein.

Figure 5:
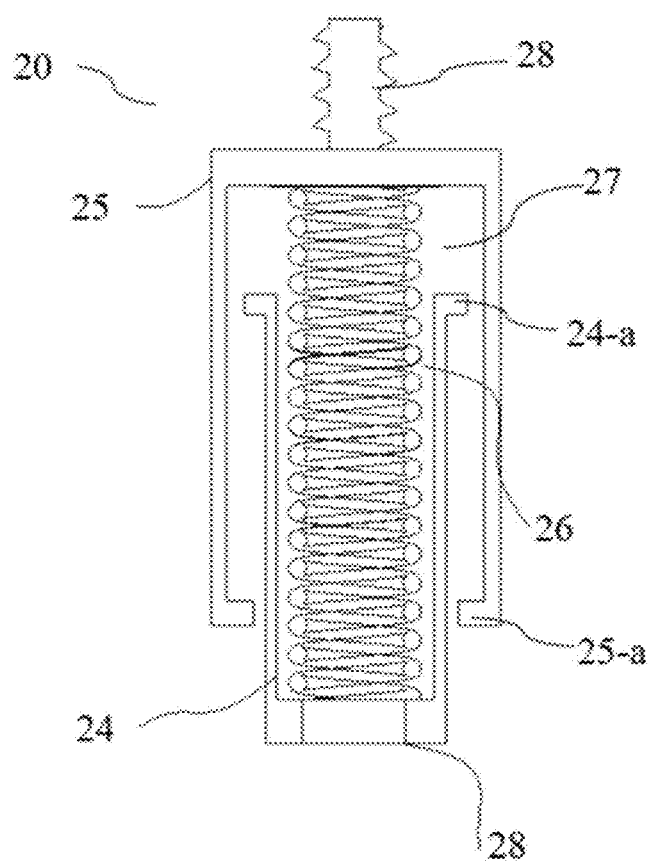
FIG. 5 is a schematic structural view of a connecting portion according to an embodiment of the present disclosure.
Figure 21:
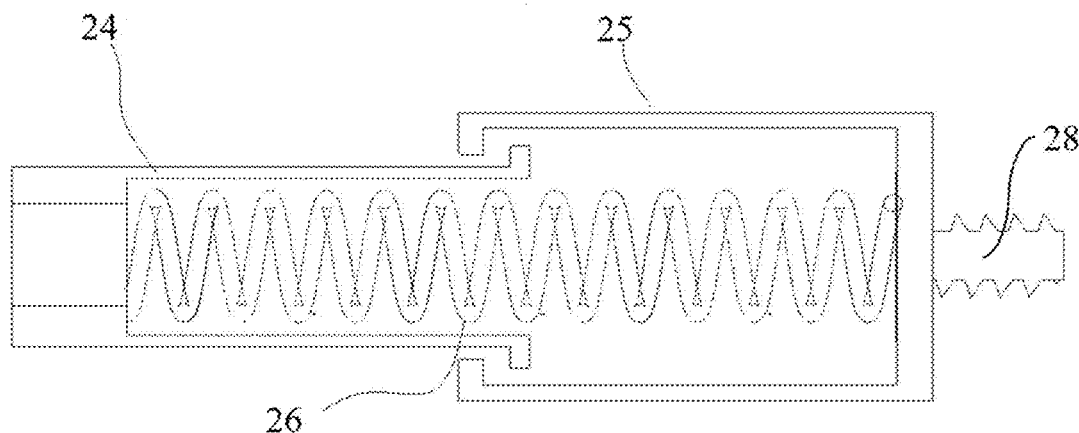
FIG. 21 is a schematic structural view of a connecting portion according to an embodiment of the present disclosure.

Specifically, as shown in FIG. 5 or FIG. 21, the connecting portion 20 includes first limiting member 24, second limiting member 25, and elastic member 26. Cavities 27 opposite to each other are respectively formed in the first limiting member 24 and the second limiting member 25. The first limiting member 24 is provided in the second limiting member 25. Gaps are provided between the first limiting member 24 and the second limiting member 25. An end of the first limiting member 24 toward the second limiting member 25 is provided with first outward-extending bent edge 24-a. An end of the second limiting member 25 toward the first limiting member 24 is provided with second inward-extending bent edge 25-a. The first bent edge 24-a and the second bent edge 25-a radially overlap partially to form an axial limiting structure.

Further, the elastic member 26 is provided between the first limiting member 24 and the second limiting member 25, with two ends respectively connected to the first limiting member 24 and the second limiting member 25. The first limiting member 24 and the second limiting member may extend or retract axially or bend relatively. Opposite ends of the first limiting member 24 and the second limiting member 25 are respectively provided with connecting structures 28. It is to be noted that an enough gap is radially reserved between the first limiting member 24 and the second limiting member 25, such that the first limiting member 24 and the second limiting member may bend. The elastic member 26 may be a spring, or an elastic metal sheet or metal wire. Two ends of the elastic member 26 are clamped or welded at opposite sides of the first limiting member and the second limiting member.

Figure 22:
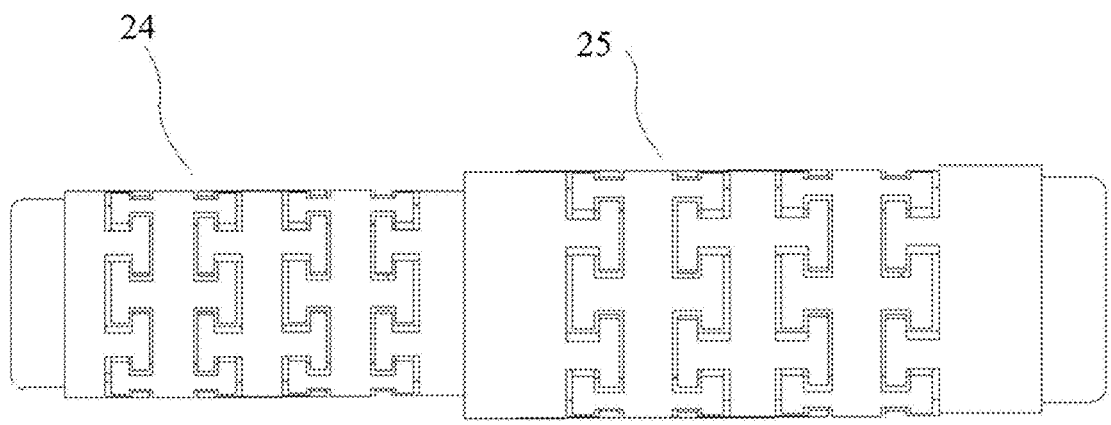
FIG. 22 is a schematic structural view of a connecting portion according to an embodiment of the present disclosure.
Figure 23:
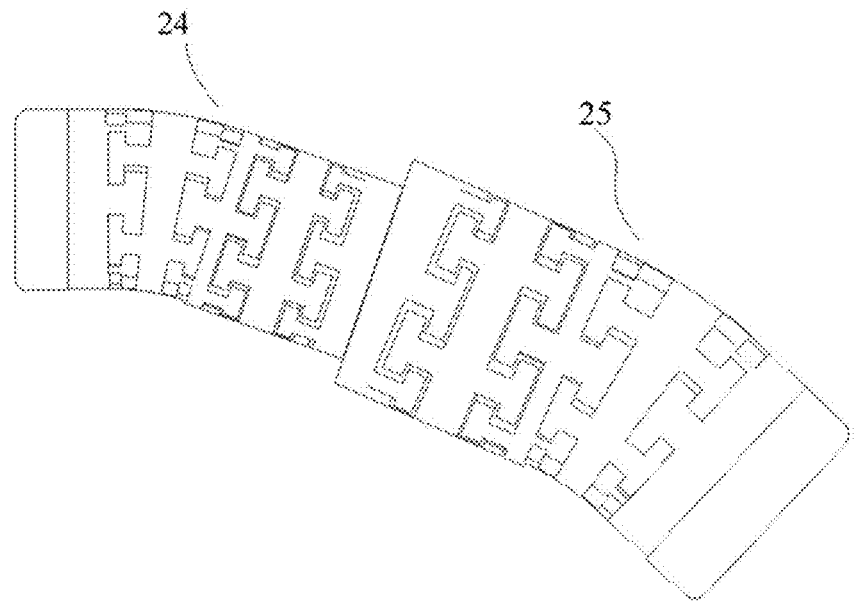
FIG. 23 is a schematic structural view of a connecting portion in FIG. 22 in a use state.

Further preferably, as shown in FIG. 22, the connecting portion 20 includes first limiting member 24, second limiting member 25, and elastic member 26. The embodiment differs from the above embodiment in: The first limiting member 24 and the second limiting member 25 each are formed by engraving a tubular member. As shown in FIG. 23, the first limiting member 24 and the second limiting member 25 have a certain bending capacity to increase an adaptability of the whole connecting portion 20.

In actual application, when the LAA opening 41 is misaligned with an implantation position of the plugging portion 10, but the plugging portion 10 is to be implanted deeply, the structure of the connecting portion 20 in the above embodiment can allow the plugging portion 10 and the covering portion 30 to present the flexibility with different axis in implantation. Therefore, the connecting portion and the covering portion are more flexible and do not affect the occlusion effect for a special structure of the LAA.

Further preferably, an end of the clamping member 23 away from the hollow limiting member 22 is provided with an external thread or an internal thread to form the plugging portion connecting structure 23-a. The first gathering member 14 is matched with the plugging portion connecting structure 23-a. An end of the threaded connector 21 away from the hollow limiting member 22 is provided with an external thread or an internal thread to form the covering portion connecting structure 21-a. The third gathering member 31 is matched with the covering portion connecting structure 21-a.

Embodiment 4

The LAA occluder in the embodiment differs from Embodiments 1-3 mainly in: A resistance member 50 is provided on the basis of the above embodiments. Contents same as above will not be repeated herein.

Specifically, as shown in FIG. 24 to FIG. 34, resistance member 50 is provided at a junction between the first gathering member 14 and the connecting portion 20 to increase a connection strength of the junction.

Figure 24:
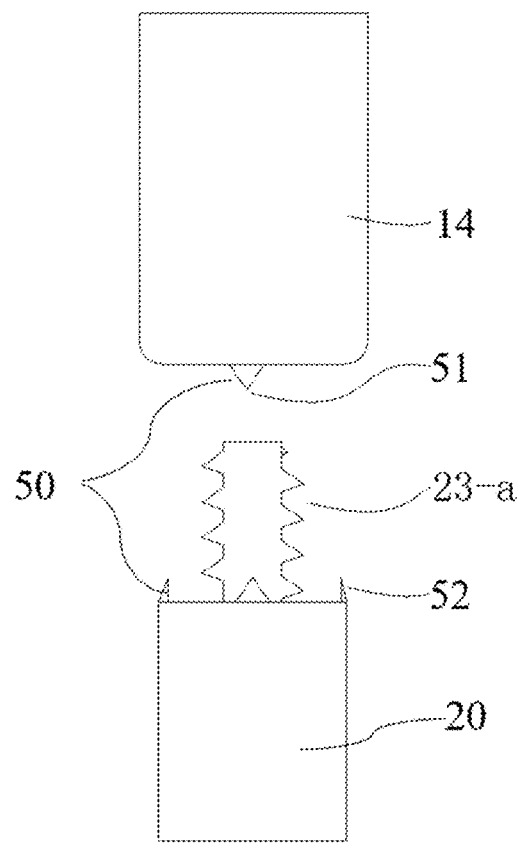
FIG. 24 is a schematic structural view of a resistance member according to an embodiment of the present disclosure.

In a preferred embodiment, as shown in FIG. 24, the resistance member 50 includes a plurality of first sawtooth-like structures 51 and a plurality of second sawtooth-like structures 52. The first sawtooth-like structures 51 are arranged at an end of the first gathering member 14 toward the connecting portion 20. The second sawtooth-like structures 52 are arranged at an end of the connecting portion 20 toward the first gathering member 14. In a connected state, the first sawtooth-like structures 51 are locked with the second sawtooth-like structures 52.

Specifically, the resistance member 50 is provided at a junction between the first gathering member 14 and the plugging portion connecting structure 23-a to make connection therebetween firmer. The resistance member 50 is approximately triangular pyramidal. One resistance member, namely the first sawtooth-like structure 51, is provided at the first gathering member 14. A plurality of resistance members, namely the second sawtooth-like structures 52, are arranged at the plugging portion connecting structure 23-a. In response to a last circle of connection between the plugging portion connecting structure 23-a and the first gathering member 14, the first sawtooth-like structure 51 comes in contact with one of the second sawtooth-like structures 52. In this case, an applied torque is increased, such that the plugging portion connecting structure 23-a is further fed, and the first sawtooth-like structure 51 is located between any two adjacent ones of the second sawtooth-like structures 52.

Figure 25:
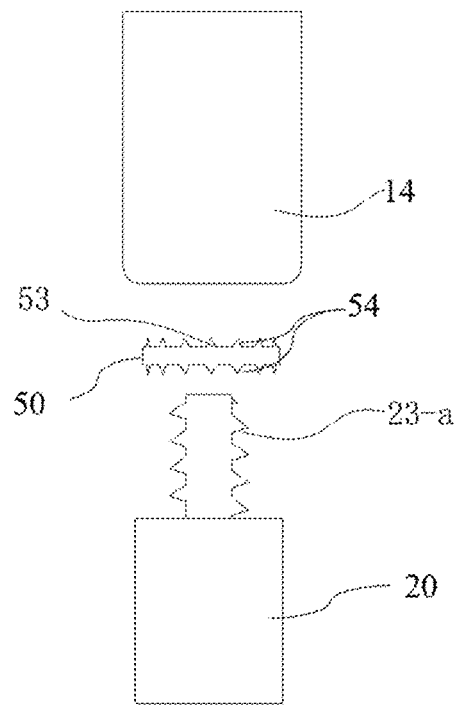
FIG. 25 is a schematic structural view of a resistance member according to an embodiment of the present disclosure.
Figure 26:
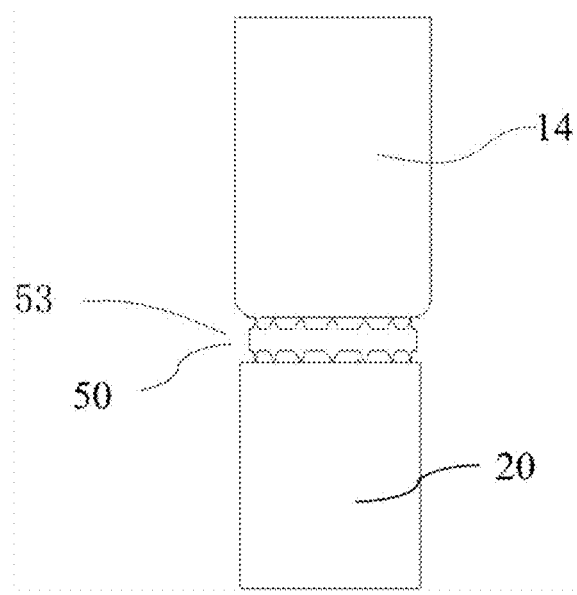
FIG. 26 is a schematic structural view of a resistance member in FIG. 25 in a connected state.

In a preferred embodiment, as shown in FIG. 25, the resistance member 50 includes resistance washer 53. The resistance washer 53 is annular, and made of biocompatible flexible material such as polyester membrane, PTFE membrane, etc. Two axial ends of the resistance washer 53 each are provided with a plurality of protrusions 54, as shown in FIG. 26. In the connected state, the resistance washer 53 is compressed by the first gathering member 14 and the connecting portion 20.

Specifically, upper and lower sections of the resistance washer 53 each are radially provided with a circle of protrusions 54 to increase a friction force between the resistance member 50 and an adjacent member. In use, the resistance member 50 is sleeved to the plugging portion connecting structure 23-a. When the plugging portion connecting structure 23-a is connected to the first gathering member 14 in place, the resistance member 50 is pressed therebetween.

Figure 27:
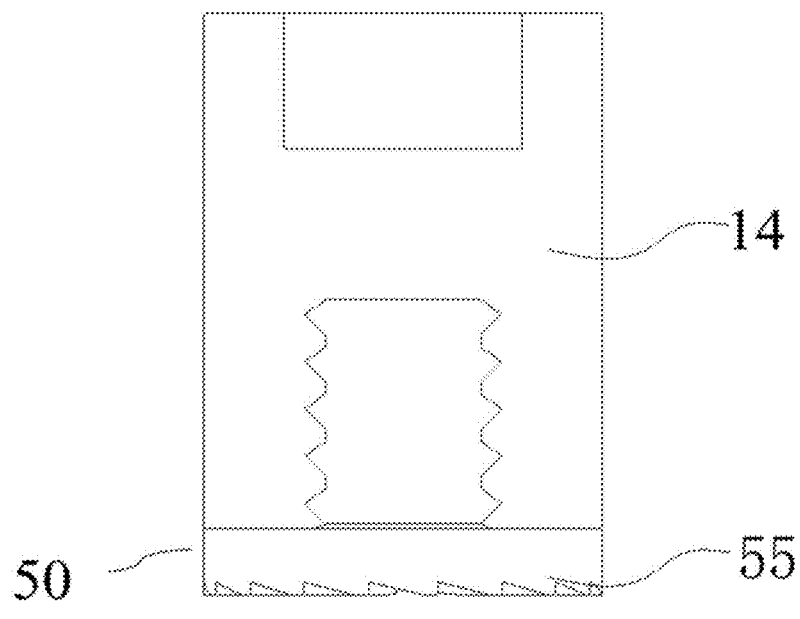
FIG. 27 is a schematic structural view of a resistance member according to an embodiment of the present disclosure.
Figure 28:
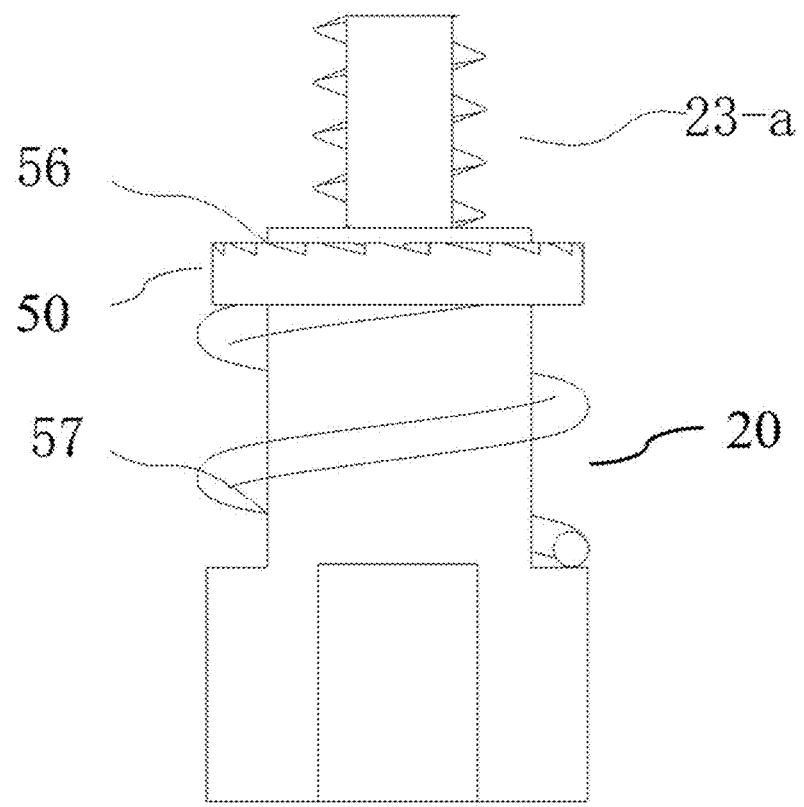
FIG. 28 is a schematic structural view of a mechanism matched with a resistance member in FIG. 27.

In another preferred embodiment, as shown in FIG. 27 and FIG. 28, the resistance member includes first resistance washer 55 and second resistance washer 56. An axial end of the first resistance washer 55 is connected to the first gathering member 14, and the other end of the first resistance washer is zigzag. The second resistance washer 56 is slidably sleeved to the connecting portion 20. An end of the second resistance washer 56 away from the plugging portion 10 is provided with spring 57, and the other end of the second resistance washer is zigzag. In the connected state, the first resistance washer 55 presses the second resistance washer 56 along the axial direction, the spring 57 is compressed axially under pressure of the second resistance washer 56, and the zigzag end of the first resistance washer 55 is engaged with the zigzag end of the second resistance washer 56.

Specifically, the first gathering member 14 and the plugging portion connecting structure 23-a each are provided with the resistance member 50, namely the first resistance washer 55 and the second resistance washer 56. The first resistance washer and the second resistance washer have the zigzag ends engaged with each other. The second resistance washer 56 is sleeved to a periphery of the plugging portion connecting structure 23-a, and makes a little relative displacement with a root of the plugging portion connecting structure 23-a to form a step. Under the resistance member of the plugging portion connecting structure 23-a, the elastic member, namely the spring 57, is provided. When the first gathering member is connected to the plugging portion connecting structure, the first resistance washer 55 and the second resistance washer 56 are engaged with each other. In this case, the elastic member is compressed to provide a support force, thereby ensuring an engaged state of the resistance member.

Figure 29:
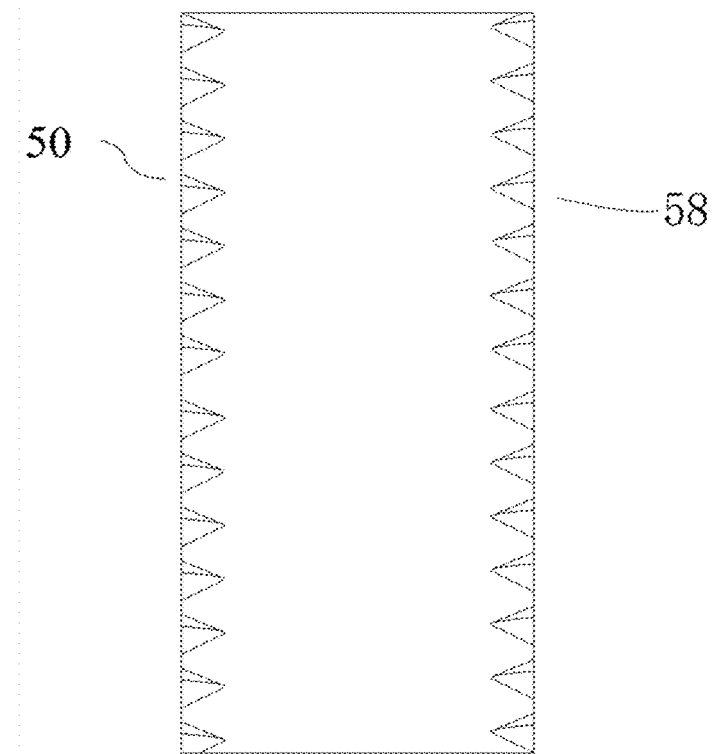
FIG. 29 is a schematic structural view of an internal threaded tube according to an embodiment of the present disclosure.
Figure 30:
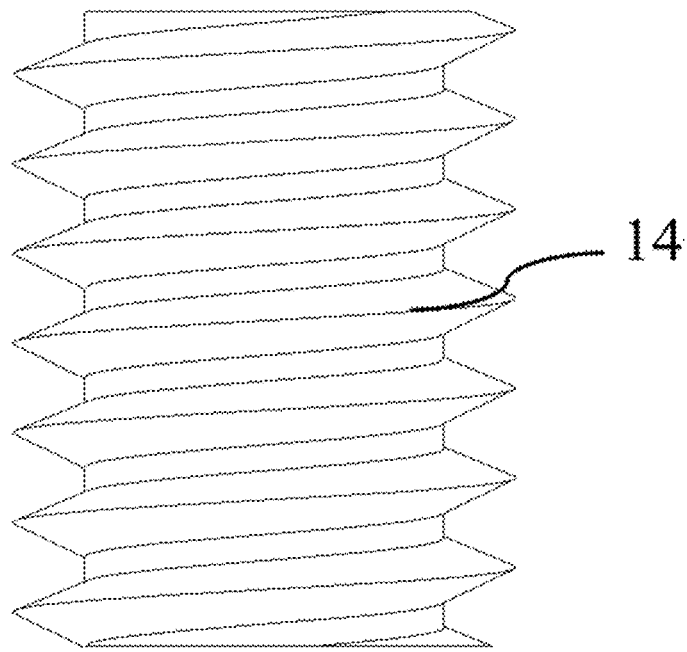
FIG. 30 is a schematic structural view of a first gathering member according to an embodiment of the present disclosure.
Figure 31:
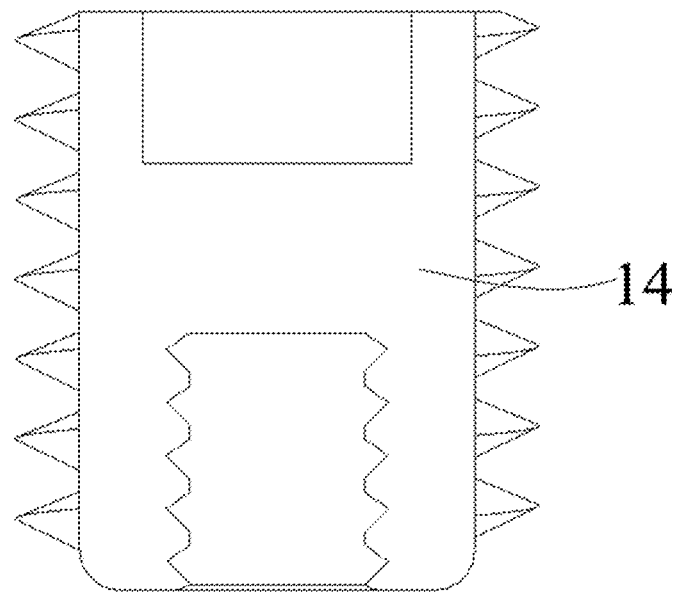
FIG. 31 is a sectional structural view in FIG. 30.
Figure 32:
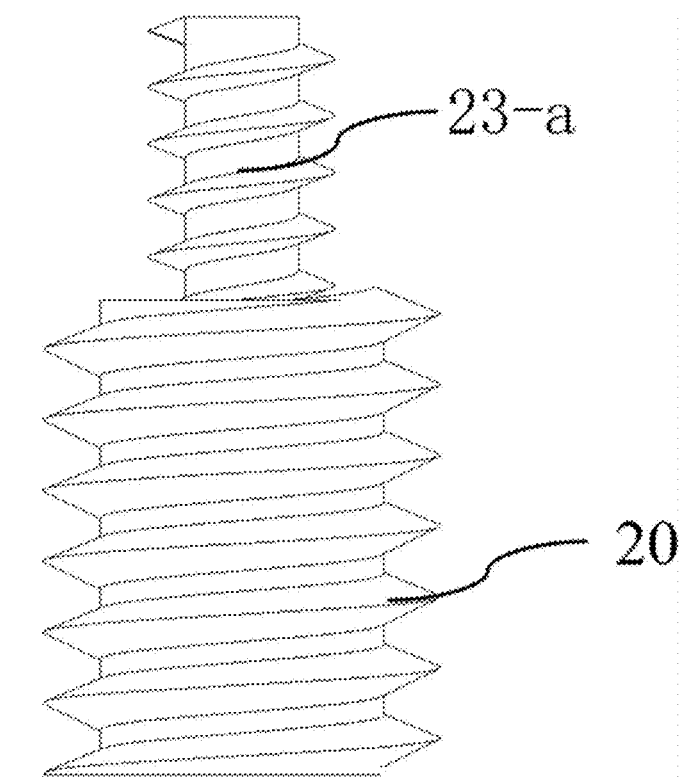
FIG. 32 is a schematic structural view of a connecting portion according to an embodiment of the present disclosure.
Figure 33:
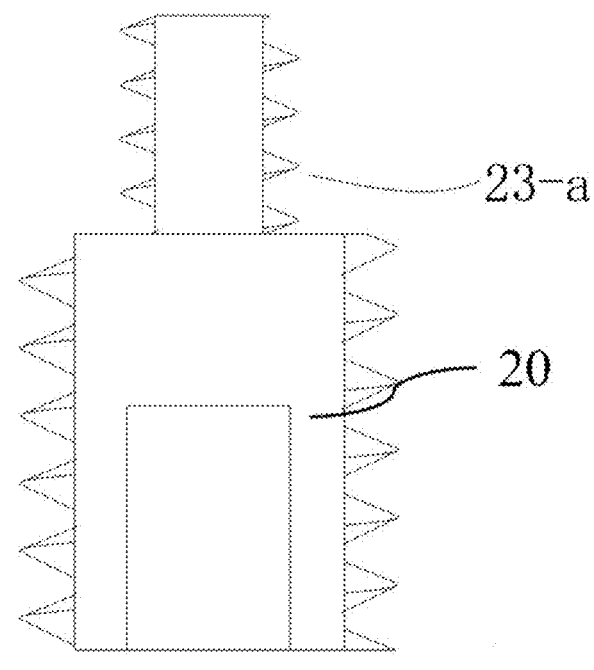
FIG. 33 is a sectional structural view in FIG. 32.
Figure 34:
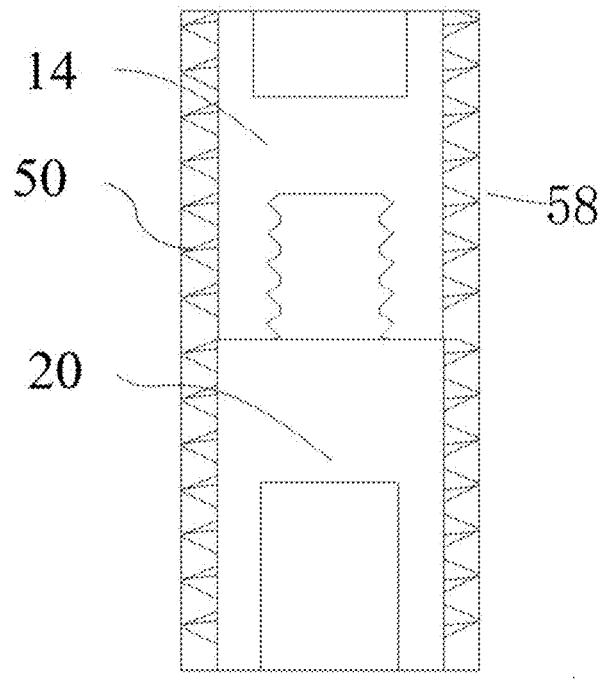
FIG. 34 is a schematic structural view of members related by FIG. 29 to FIG. 33 in a connected state.

In another preferred embodiment, as shown in FIG. 29, the resistance member 50 includes internal threaded tube 58. In the connected state, the internal threaded tube 58 is sleeved to the first gathering member 14 and the connecting portion 20. As shown in FIG. 30 to FIG. 34, external threads matched with the internal threaded tube 58 are respectively provided on a surface of the first gathering member 14 and a surface of the connecting portion 20. Therefore, the plugging portion 10 and the connecting portion 20 are connected more reliably. At an implantation position, even by external force, for example, the pushing device 60 is separated from the pushing device connection position 32-a of the covering portion 30 in rotation, the connection between the plugging portion 10 and the covering portion 30 is not affected.

It is to be noted that the connected state refers to a state in which the LAA occluder is delivered by the pushing device. In response to the independent use of the plugging portion, the connected state refers to a state in which the plugging portion 10 is directly butted with the pushing device In response to the combined use of the plugging portion, the connected state refers to a state in which the plugging portion 10, the connecting portion 20 and the covering portion 30 are connected sequentially. In this state, the pushing device 60 is butted with the covering portion 30. In addition, the resistance member may further be provided at a junction between the connecting portion 20 and the covering portion 30.

Embodiment 5

The embodiment provides a method of application for an LAA occluder, which is applied to the LAA occluder in any one of the above embodiments.

An LAA anatomy is evaluated with an ultrasonography, and then an appropriate usage mode and an appropriate size of the LAA occluder are selected.

Figure 35:
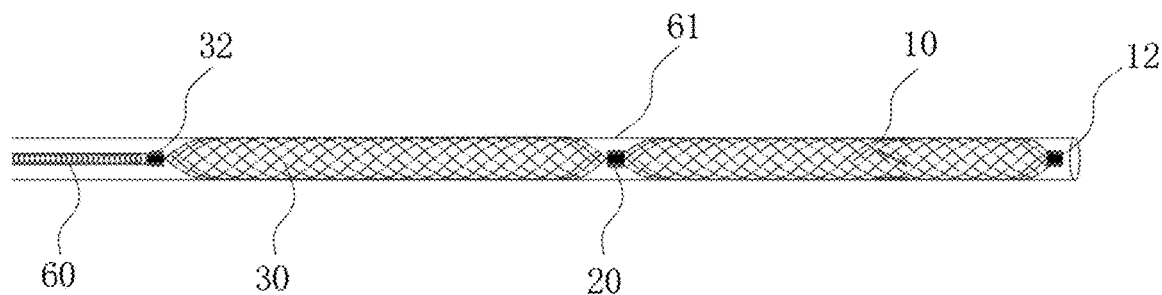
FIG. 35 is a schematic structural view in combined use of an plugging portion according to the present disclosure.

Specifically, in a case where an implantation position of the plugging portion 10 is apart from an LAA opening and an obvious residual cavity near an LAA opening 41 cannot be sealed, the method of application includes the following use steps:

Step 1: As shown in FIG. 35, the plugging portion 10, the connecting portion 20 and the covering portion 30 are connected sequentially. An end of the covering portion 30 away from the connecting portion 20 is connected with the pushing device 60. The covering portion 30 and the plugging portion 10 are stretched to transform into linear shape. The pushing device 60 pushes the LAA occluder to a human body through delivery sheath 61.

Figure 36:
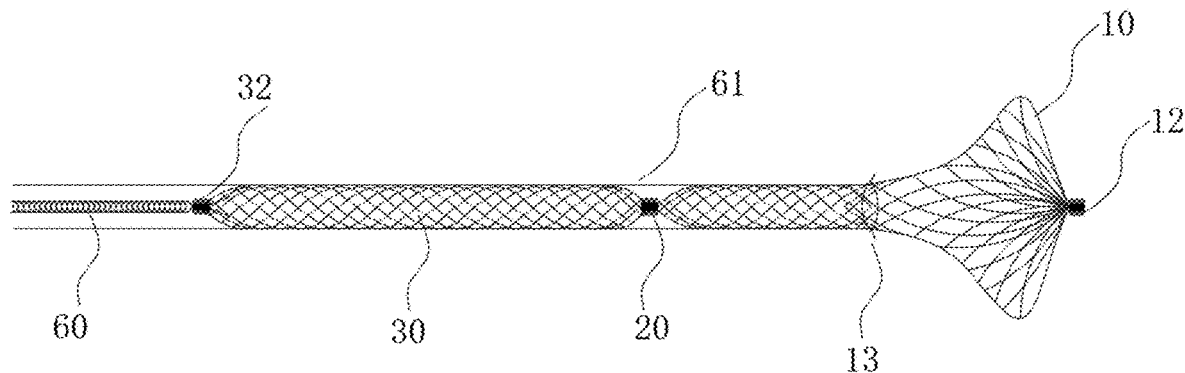
FIG. 36 is a schematic structural view of a subsequent step in FIG. 35.
Figure 37:
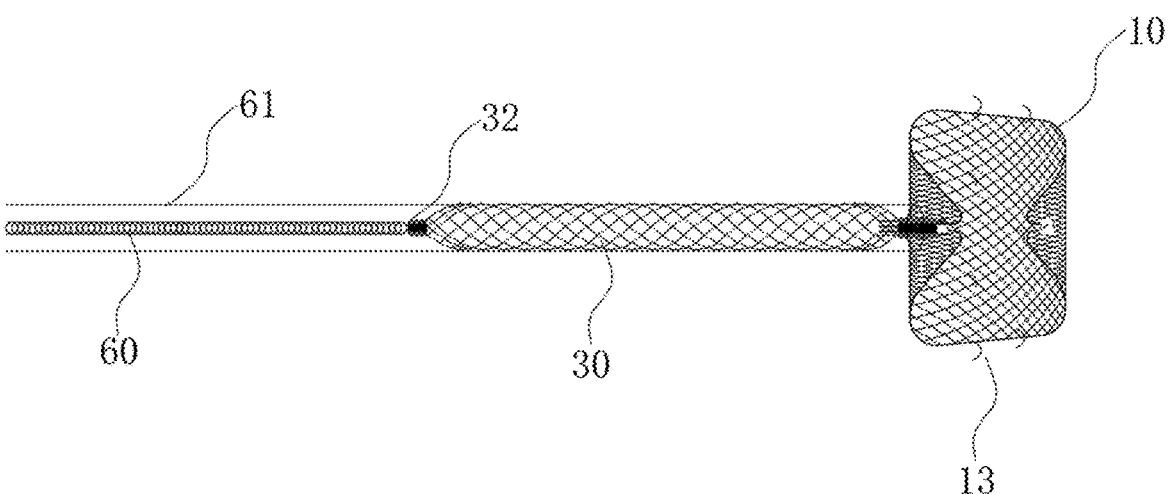
FIG. 37 is a schematic structural view of a subsequent step in FIG. 36.

Step 2: As shown in FIG. 36 and FIG. 37, at the implantation position, the plugging portion is pushed out of the delivery sheath 61, and the support mesh of the plugging portion 10 away from the connecting portion 20 expands gradually to form a small plane for pre-targeting. A remaining part of the support mesh expands sequentially, such that the plugging portion 10 gradually attaches to LAA tissues. The anchoring members 13 expand at the same time to grasp LAA tissues.

Figure 38:
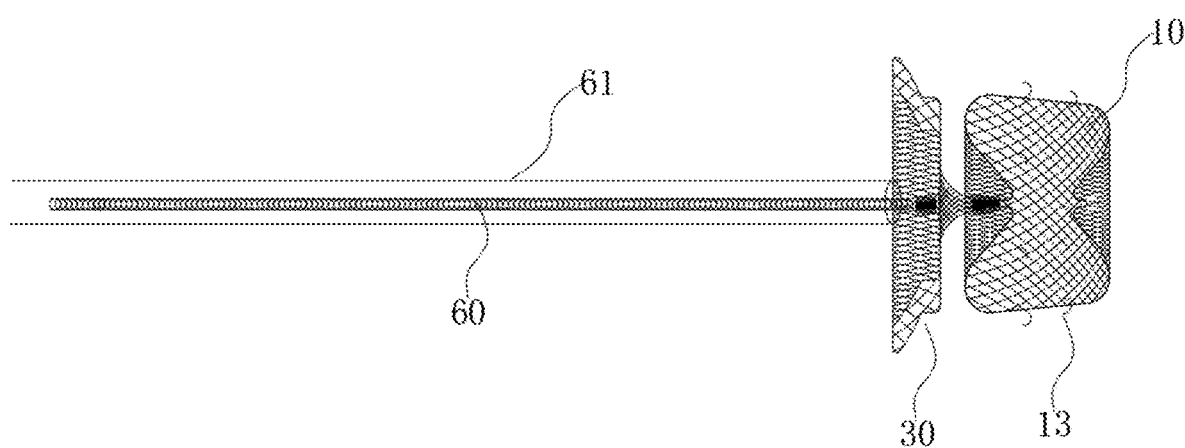
FIG. 38 is a schematic structural view of a subsequent step in FIG. 37.

Step 3: As shown in FIG. 38, the connecting portion 20 and the covering portion 30 are sequentially pushed out of the delivery sheath 61, such that the covering portion 30 expands to cover the LAA opening 41.

In other words, the LAA anatomy is often evaluated with the ultrasonography first, and then the appropriate LAA occluder is used for a surgery. When the implantation position of the plugging portion 10 is apart from the LAA opening 41, and an obvious residual cavity near the LAA opening 41 cannot be sealed, the plugging portion 10 is used in combination with the covering portion 30. Two ends of the connecting portion 20 are respectively in threaded connection with the plugging portion 10 and the covering portion 30. The support mesh of the covering portion 30 and the support mesh of the plugging portion 10 are stretched to transform into linear shape. The occluder in linear shape is pushed to the human body through the elongated delivery sheath 61. At the implantation position, the end of the plugging portion 10 away from the connecting portion 20 is pushed out of the delivery sheath 61, and the fourth gathering member 12 is pushed out first. The support mesh near the fourth gathering member 12 is gradually formed into a plane with a small radial profile. The plugging portion 10 with a distal end being a plane further expands gradually in the LAA. This can effectively prevent potential damages to LAA tissues by the occluder, and can be applied to the LAA with different structures more widely. While the plugging portion 10 is further pushed out, the plugging portion 10 gradually attaches to LAA tissues. The anchoring members 13 expand to grasp LAA tissues. There is no damage to LAA tissues in the grasping. At last, the covering portion 30 is pushed out to cover the LAA opening 41.

Further preferably, when an implantation position of the plugging portion 10 is close to the LAA opening, and the plugging portion 10 may basically seal the LAA opening 41 without a residual cavity, the method of application includes the following steps:

Step 1: The plugging portion 10 is connected to the pushing device 60. The covering portion 30 is stretched to transform into linear shape. The pushing device 60 pushes the LAA occluder to a human body through the delivery sheath 61.

Step 2: At the implantation position, the plugging portion 10 is pushed out of the delivery sheath 61, and the support mesh of the plugging portion 10 away from the connecting portion 20 expands gradually to form a small plane for pre-targeting. A remaining part of the support mesh expands sequentially, such that the plugging portion 10 gradually attaches to LAA tissues. The anchoring members 13 expand to grasp LAA tissues.

Step 3: The pushing device 60 is operated, such that the pushing device 60 is separated from the plugging portion 10, and the plugging portion 10 is used individually to seal the LAA opening 41.

In other words, when the implantation position of the plugging portion 10 is close to the LAA opening 41, and the LAA opening 41 may be basically sealed by the plugging portion 10 without the residual cavity, the plugging portion 10 may be used individually. The pushing device 60 is connected to the plugging portion 10. The LAA occluder is implanted into the LAA, as shown in FIG. 11 and FIG. 13. There is no residual cavity at the LAA opening 41, and the channel between the LAA and the LA is occluded.

In actual application, in case of an inappropriate size of the occluder, the occluder can be retracted to the delivery sheath 61 to change an appropriate size for reimplantation. When the plugging portion 10 is used in combination with the covering portion 30, there may be a case where the plugging portion 10 or the covering portion 30 has an appropriate portion and an inappropriate portion. In this case, replacement may be made only to the inappropriate portion for reimplantation. Therefore, with the detachable segment-wise design, the LAA occluder can be selected flexibly, achieves the better occlusion effect and shortens the time of operation.

The above are merely preferred implementations of the present disclosure. It should be noted that several improvements and modifications may further be made by a person of ordinary skill in the art without departing from the principle of the present disclosure, and such improvements and modifications should also be deemed as falling within the protection scope of the present disclosure.

What is claimed is:

1. A left atrial appendage (LAA) occluder, comprising a plugging portion, a connecting portion, and a covering portion that are connected sequentially along an axial direction, wherein
the plugging portion comprises a first gathering member and a first support mesh that can be transformed to have a reduced radial profile; a plurality of anchoring members for grasping LAA tissues are arranged on outer peripheral surface of the first support mesh; the first gathering member is provided at an end of the first support mesh close to the connecting portion; and the first gathering member is detachably connected to the connecting portion;
the covering portion comprises a second gathering member and a second support mesh that can be transformed to have a reduced radial profile; in a natural state, radial profile of the covering portion is not less than radial profile of the plugging portion; the second gathering member is provided at an end of the second support mesh away from the connecting portion; and an end of the first gathering member away from the first support mesh and an end of the second gathering member away from the first support mesh are respectively provided with pushing device connection positions, such that the plugging portion has two usage modes;
in response to an independent use of the plugging portion, the plugging portion is disconnected from the connecting portion, and a pushing device can be connected with an end of the first gathering member away from the plugging portion; and
in response to a combined use of the plugging portion, the plugging portion is detachably connected to the covering portion through the connecting portion, and the pushing device can be connected with an end of the second gathering member away from the covering portion.

2. The LAA occluder according to claim 1, wherein
the connecting portion comprises a threaded connector, a hollow limiting member, and a clamping member; and the hollow limiting member has two open ends, and is provided therein with a spherical cavity;
one end of the clamping member is rotatably provided in the spherical cavity and matched with the spherical cavity, and the other end is provided with a plugging portion connecting structure; and
one end of the threaded connector is slidably provided in the hollow limiting member and coaxial with the hollow limiting member, and the other end is provided with a covering portion connecting structure.

3. The LAA occluder according to claim 1, wherein
the connecting portion comprises a first limiting member, a second limiting member, and an elastic member;
cavities opposite to each other are respectively formed in the first limiting member and the second limiting member; the first limiting member is spaced apart in the second limiting member; a side of the first limiting member toward the second limiting member is provided with a first outward-extending bent edge; a side of the second limiting member toward the first limiting member is provided with a second inward-extending bent edge; and the first bent edge and the second bent edge radially overlap partially to form an axial limiting structure;
the elastic member is provided between the first limiting member and the second limiting member, with two ends respectively connected to the first limiting member and the second limiting member; and the first limiting member and the second limiting member extend or retract axially or bend relatively; and
opposite sides of the first limiting member and the second limiting member are respectively provided with connecting structures.

4. The LAA occluder according to claim 1, wherein
the plugging portion comprises a fourth gathering member; and the fourth gathering member is provided at an end of the first support mesh away from the connecting portion;

the first support mesh comprises a plurality of elastic metal wires; the elastic metal wires are interweaved with each other to form a hollow cylindrical structure; two axial ends of the first support mesh are gathered, and are respectively sealed by the first gathering member and the fourth gathering member; the first gathering member and the fourth gathering member approach each other, such that two axial ends of the plugging portion are recessed; and the first gathering member is provided with a thread structure to match the connecting portion; or, the plugging portion comprises support rods formed by engraving an elastic metal tube; and two axial ends of the plugging portion are gathered, and are respectively sealed by the first gathering member and the fourth gathering member; or, only an end of the plugging portion close to the connecting portion is sealed by the first gathering member, and the first gathering member is provided with a thread structure to match the connecting portion; or, the plugging portion is a cylinder having two axial ends with basically same radial profiles.

5. The LAA occluder according to claim 1, wherein
the covering portion comprises a third gathering member; the third gathering member is provided at an end of the second support mesh close to the connecting portion; and the connecting portion is detachably connected to the covering portion through the third gathering member;

the second support mesh comprises a plurality of elastic metal wires; the elastic metal wires are interweaved with each other to form a hollow flat structure; two axial ends of the second support mesh are gathered, and are respectively sealed by the second gathering member and the third gathering member; the second gathering member and the third gathering member are coaxial with the covering portion; and a center of an end of the covering portion towards the connecting portion is convex, and is sealed by the third gathering member;

and/or, polymer membranes are respectively provided in the plugging portion and the covering portion.

6. The LAA occluder according to claim 2, wherein
an end of the clamping member away from the hollow limiting member is provided with an external thread or an internal thread to form the plugging portion connecting structure, and the first gathering member is matched with the plugging portion connecting structure;

and/or, an end of the threaded connector away from the hollow limiting member is provided with an external thread or an internal thread to form the covering portion connecting structure.

7. The LAA occluder according to claim 1, wherein
the anchoring members each comprises a free end and a fixed end; the fixed end is fixedly connected to the plugging portion, while the free end extends outward; and the plurality of anchoring members surround the outer peripheral surface of the plugging portion;

the anchoring members each has a length of 1-4 mm;

the plurality of anchoring members are respectively located at edges of 1-3 cross sections of the plugging portion; and each cross sections' edge is provided with 4-10 anchoring members; and when the anchoring members are not located on a same cross section, the anchoring members are misaligned along a radial direction of the plugging portion.

8. The LAA occluder according to claim 1, wherein
a resistance member is provided at a junction between the first gathering member and the connecting portion to increase a connection strength of the junction;

the resistance member comprises a first sawtooth-like structure and a plurality of second sawtooth-like structures; the first sawtooth-like structure is arranged at an end of the first gathering member toward the connecting portion; the second sawtooth-like structures are arranged at an end of the connecting portion toward the first gathering member; and in a connected state, the first sawtooth-like structure is locked with the second sawtooth-like structures;

or, the resistance member comprises a resistance washer; the resistance washer is annular, and made of biocompatible flexible material such as polyester membrane or polytetrafluoroethylene (PTFE) membrane; two axial ends of the resistance washer each are provided with a plurality of protrusions; and in the connected state, the resistance washer is compressed between the first gathering member and the connecting portion.

9. The LAA occluder according to claim 8, wherein
the resistance member comprises a first resistance washer and a second resistance washer; an axial end of the first resistance washer is connected to the first gathering member, and the other end of the first resistance washer is zigzag; the second resistance washer is slidably sleeved outside the connecting portion; an end of the second resistance washer away from the plugging portion is provided with a spring, and the other end of the second resistance washer is zigzag; and in the connected state, the first resistance washer presses the second resistance washer along the axial direction, the spring is compressed axially under a pressure of the second resistance washer, and the zigzag end of the first resistance washer is engaged with the zigzag end of the second resistance washer;

or, the resistance member comprises an internal threaded tube; in the connected state, the internal threaded tube is sleeved outside the first gathering member and the connecting portion; and external threads matched with the internal threaded tube are respectively provided on a surface of the first gathering member and a surface of the connecting portion.

10. A method of application for a left atrial appendage (LAA) occluder, applied to the LAA occluder according to claim 1, and comprising:

detecting an LAA anatomy of a patient, wherein
in a case where an implantation position of the plugging portion is apart from an LAA opening, and an obvious residual cavity near the LAA opening is not sealed, the method of application comprises the following steps:

step 1: sequentially connecting the plugging portion, the connecting portion and the covering portion, providing an end of the covering portion away from the connecting portion on a tip of the pushing device, stretching the covering portion and the plugging portion to transform into a linear shape, and allowing the pushing device to push the LAA occluder to a human body through a delivery sheath;

step 2: pushing, at the implantation position, the plugging portion out of the delivery sheath, wherein the first support mesh of the plugging portion away from the connecting portion expands gradually to form a small plane for pre-targeting; a remaining part of the first support mesh expands sequentially, such that the plugging portion gradually attaches to LAA tissues; and the anchoring members expand at the same time to grasp the LAA tissues; and step 3: sequentially pushing the connecting portion and the covering portion out of the delivery sheath, wherein the covering portion expands to cover the LAA opening.

11. The method of application according to claim 10, wherein in a case where an implantation position of the plugging portion is close to the LAA opening, and the plugging portion basically seals the LAA opening without the residual cavity, the method of application comprises the following steps:

step 1: connecting the plugging portion to the pushing device through the first gathering member, stretching the covering portion to transform into a linear shape, and allowing the pushing device to push the LAA occluder to a human body through the delivery sheath;

step 2: gradually pushing, at the implantation position, the plugging portion out of the delivery sheath, wherein the first support mesh of the plugging portion away from the connecting portion expands gradually to form a small plane for pre-targeting; a remaining part of the first support mesh expands sequentially, such that the plugging portion gradually attaches to LAA tissues; and the anchoring members expand at the same time to grasp the LAA tissues; and step 3: operating the pushing device, such that the pushing device is separated from the plugging portion, and the plugging portion is used individually to seal the LAA opening.

12. The method of application according to claim 10, wherein in the LAA occluder, the connecting portion comprises a threaded connector, a hollow limiting member, and a clamping member; and the hollow limiting member has two open ends, and is provided therein with a spherical cavity;

one end of the clamping member is rotatably provided in the spherical cavity and matched with the spherical cavity, and the other end is provided with a plugging portion connecting structure; and one end of the threaded connector is slidably provided in the hollow limiting member and coaxial with the hollow limiting member, and the other end is provided with a covering portion connecting structure.

13. The method of application according to claim 10, wherein in the LAA occluder, the connecting portion comprises a first limiting member, a second limiting member, and an elastic member;

cavities opposite to each other are respectively formed in the first limiting member and the second limiting member; the first limiting member is spaced apart in the second limiting member; a side of the first limiting member toward the second limiting member is provided with a first outward-extending bent edge; a side of the second limiting member toward the first limiting member is provided with a second inward-extending bent edge; and the first bent edge and the second bent edge radially overlap partially to form an axial limiting structure;

the elastic member is provided between the first limiting member and the second limiting member, with two ends respectively connected to the first limiting member and the second limiting member; and the first limiting member and the second limiting member extend or retract axially or bend relatively; and opposite sides of the first limiting member and the second limiting member are respectively provided with connecting structures.

14. The method of application according to claim 10, wherein in the LAA occluder, the plugging portion comprises a fourth gathering member; and the fourth gathering member is provided at an end of the first support mesh away from the connecting portion;

the first support mesh comprises a plurality of elastic metal wires; the elastic metal wires are interweaved with each other to form a hollow cylindrical structure; two axial ends of the first support mesh are gathered, and are respectively sealed by the first gathering member and the fourth gathering member; the first gathering member and the fourth gathering member approach each other, such that two axial ends of the plugging portion are recessed; and the first gathering member is provided with a thread structure to match the connecting portion; or, the plugging portion comprises support rods formed by engraving an elastic metal tube; and two axial ends of the plugging portion are gathered, and are respectively sealed by the first gathering member and the fourth gathering member; or, only an end of the plugging portion close to the connecting portion is sealed by the first gathering member, and the first gathering member is provided with a thread structure to match the connecting portion; or, the plugging portion is a cylinder having two axial ends with basically same radial profiles.

15. The method of application according to claim 10, wherein in the LAA occluder, the covering portion comprises a third gathering member; the third gathering member is provided at an end of the second support mesh close to the connecting portion; and the connecting portion is detachably connected to the covering portion through the third gathering member;

the second support mesh comprises a plurality of elastic metal wires; the elastic metal wires are interweaved with each other to form a hollow flat structure; two axial ends of the second support mesh are gathered, and are respectively sealed by the second gathering member and the third gathering member; the second gathering member and the third gathering member are coaxial with the covering portion; and a center of an end of the covering portion towards the connecting portion is convex, and is sealed by the third gathering member; and/or, polymer membranes are respectively provided in the plugging portion and the covering portion.

16. The method of application according to claim 12, wherein in the LAA occluder, an end of the clamping member away from the hollow limiting member is provided with an external thread or an internal thread to form the plugging portion connecting structure, and the first gathering member is matched with the plugging portion connecting structure;

and/or, an end of the threaded connector away from the hollow limiting member is provided with an external thread or an internal thread to form the covering portion connecting structure.

17. The method of application according to claim 10, wherein in the LAA occluder,
 the anchoring members each comprises a free end and a fixed end; the fixed end is fixedly connected to the plugging portion, while the free end extends outward; and the plurality of anchoring members surround the outer peripheral surface of the plugging portion;
 the anchoring members each has a length of 1-4 mm;
 the plurality of anchoring members are respectively located at edges of 1-3 cross sections of the plugging portion; and each cross sections' edge is provided with 4-10 anchoring members; and
 when the anchoring members are not located on a same cross section, the anchoring members are misaligned along a radial direction of the plugging portion.

18. The method of application according to claim 10, wherein in the LAA occluder,
 a resistance member is provided at a junction between the first gathering member and the connecting portion to increase a connection strength of the junction;
 the resistance member comprises a first sawtooth-like structure and a plurality of second sawtooth-like structures; the first sawtooth-like structure is arranged at an end of the first gathering member toward the connecting portion; the second sawtooth-like structures are arranged at an end of the connecting portion toward the first gathering member; and in a connected state, the first sawtooth-like structure is locked with the second sawtooth-like structures;
 or,
 the resistance member comprises a resistance washer; the resistance washer is annular, and made of biocompatible flexible material such as polyester membrane or polytetrafluoroethylene (PTFE) membrane; two axial ends of the resistance washer each are provided with a plurality of protrusions; and in the connected state, the resistance washer is compressed between the first gathering member and the connecting portion.

19. The method of application according to claim 18, wherein in the LAA occluder,
 the resistance member comprises a first resistance washer and a second resistance washer; an axial end of the first resistance washer is connected to the first gathering member, and the other end of the first resistance washer is zigzag; the second resistance washer is slidably sleeved outside the connecting portion; an end of the second resistance washer away from the plugging portion is provided with a spring, and the other end of the second resistance washer is zigzag; and in the connected state, the first resistance washer presses the second resistance washer along the axial direction, the spring is compressed axially under a pressure of the second resistance washer, and the zigzag end of the first resistance washer is engaged with the zigzag end of the second resistance washer;
 or,
 the resistance member comprises an internal threaded tube; in the connected state, the internal threaded tube is sleeved outside the first gathering member and the connecting portion; and external threads matched with the internal threaded tube are respectively provided on a surface of the first gathering member and a surface of the connecting portion.

* * * * *